(12) United States Patent
Sanchez

(10) Patent No.: US 11,571,359 B2
(45) Date of Patent: Feb. 7, 2023

(54) STORAGE/CONTAINMENT UNIT FOR FLEXIBLE POUCH FILLED WITH BIOPHARMACEUTICAL FLUID, AND METHOD OF ASSEMBLING A FREEZE/THAW CONTAINMENT SYSTEM, USING A PROTECTING BODY

(71) Applicant: SARTORIUS STEDIM NORTH AMERICA, Bohemia, NY (US)

(72) Inventor: Marc Sanchez, Brooklyn, NY (US)

(73) Assignee: SARTORIUS STEDIM NORTH AMERICA, Bohemia, NY (US)

( * ) Notice: Subject to any disclaimer, the term of this patent is extended or adjusted under 35 U.S.C. 154(b) by 224 days.

(21) Appl. No.: 16/943,671

(22) Filed: Jul. 30, 2020

(65) Prior Publication Data
US 2022/0031566 A1 Feb. 3, 2022

(51) Int. Cl.
  *A61J 1/16* (2006.01)
  *A61J 1/14* (2006.01)
  *A61J 1/10* (2006.01)

(52) U.S. Cl.
  CPC . *A61J 1/16* (2013.01); *A61J 1/10* (2013.01); *A61J 1/1468* (2015.05); *A61J 1/1475* (2013.01)

(58) Field of Classification Search
  CPC ......... A61B 50/00; A61B 50/30; A61B 50/31; A61J 1/1475; A61J 1/10; A61J 1/1468; A61J 1/16

USPC .................................................. 206/438, 370
See application file for complete search history.

(56) References Cited

U.S. PATENT DOCUMENTS

| | | | |
|---|---|---|---|
| 2012/0152943 A1 | 6/2012 | Leoncavallo et al. | |
| 2015/0374583 A1 | 12/2015 | Pavlik | |
| 2018/0125757 A1 | 5/2018 | Sanchez et al. | |
| 2018/0128707 A1* | 5/2018 | Sanchez | G01M 3/3218 |

FOREIGN PATENT DOCUMENTS

| | | |
|---|---|---|
| EP | 2 322 442 | 5/2011 |
| WO | 03/037082 | 5/2003 |
| WO | 2015/200218 | 12/2015 |

* cited by examiner

*Primary Examiner* — King M Chu
(74) *Attorney, Agent, or Firm* — Nixon & Vanderhye

(57) ABSTRACT

A freeze/thaw containment system is provided, having a protecting body and a flexible pouch protected by two plates of the protecting body. The two plates are attached together at a peripheral margin and form a rectangular protecting body. The peripheral margin is mounted in supporting parts of a stationary frame and sliding positioning members are secured to the peripheral margin, so that the peripheral margin is guided and allowed to be displaced inwardly during filling of the pouch, while the protecting body extends generally planar to sandwich and constrain the pouch in empty state of the pouch. This way of holding and retaining the protecting body allows for progressive conformational change of the protecting body due to the change in volume of the pouch when filled with a biopharmaceutical product, while facilitating reverse displacement of the peripheral margin during draining operations.

20 Claims, 19 Drawing Sheets

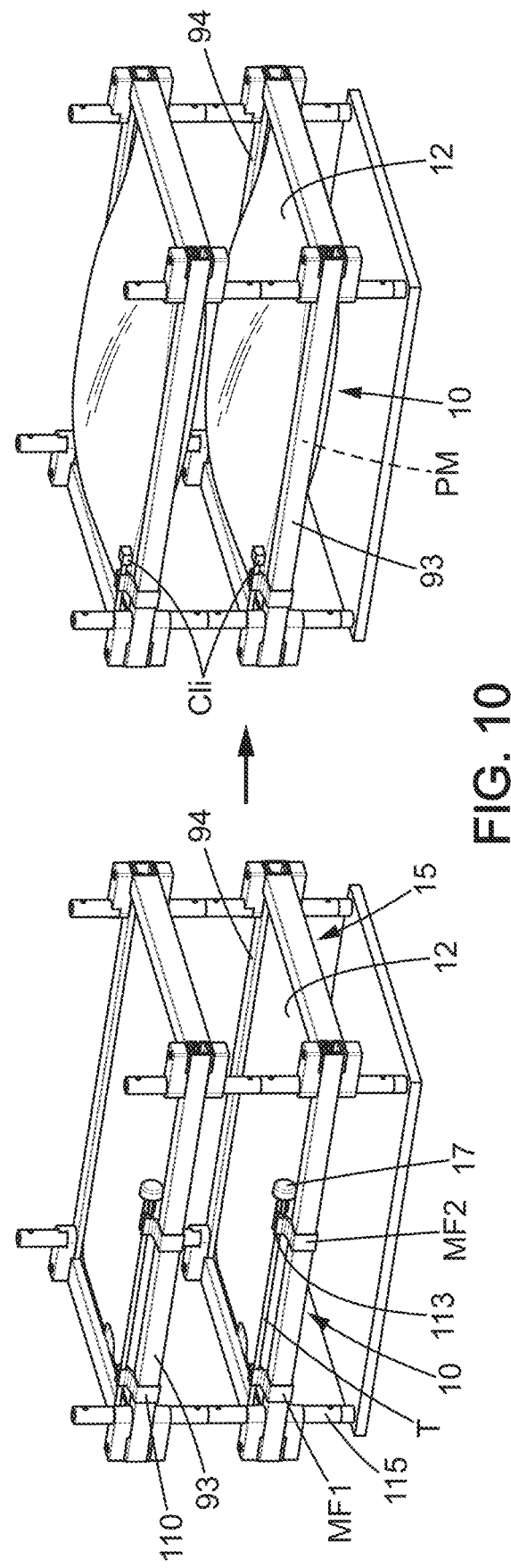

STORAGE/CONTAINMENT UNIT FOR FLEXIBLE POUCH FILLED WITH BIOPHARMACEUTICAL FLUID, AND METHOD OF ASSEMBLING A FREEZE/THAW CONTAINMENT SYSTEM, USING A PROTECTING BODY

BACKGROUND OF THE INVENTION

Field of the Invention

The present invention generally relates to the protection of a flexible pouch specially designed to contain a biopharmaceutical fluid and more broadly to a system for containing a biopharmaceutical fluid. The invention also relates to methods for manufacturing/assembling such a system that is adapted for freezing and thawing the biopharmaceutical fluid within the system. A biopharmaceutical fluid means a biotechnological derived fluid, for example a fluid derived from a culture medium, a cell culture, a buffer solution, an artificial nutrition liquid, a blood fraction, a blood derived component or a pharmaceutical fluid or, more broadly, a fluid specifically designed to be used in the medical field. Of course, the fluid may become solid or partly solid after freezing (typically at a temperature much lower than 0° C.).

Description of Related Art

It is known to use a flexible pouch to contain biopharmaceutical fluid. The flexible pouch is able to withstand low mechanical stress without damage. Hence, the leakage risk is reduced. Moreover, the flexible pouch is advantageous since it can be folded or stored flat when there is no biopharmaceutical fluid inside. Hence, the flexible pouch occupies a small volume.

The flexible pouch is generally designed for a single use and to contain a biopharmaceutical fluid volume which is between 1 liter and 500 liters.

However, specifically for shipping of the flexible pouch filled with fluid, for example, between several plant areas or from the provider of the fluid to its client which will use it, but also for storage, the flexible pouch must be protected, although the leakage risk is small.

The document EP-2 322 442 discloses a container for a flexible pouch. The container comprises a lower part and an upper part which are rigid and joined along a common edge and which form a single piece container. The container has a volume which is much more important than the volume of the flexible pouch. Consequently, the container has a useless volume. Moreover, if the flexible pouch is not retained by suitable positioning means provided in the container, it could be moved within the container, especially during shipping. Thus, the leakage risk increases.

Single-use polymeric containers, hereafter called bags or pouches, are successfully used for the storage of biopharmaceuticals in liquid state. Today, bags made of ethylene vinyl acetate (EVA) or low-density polyethylene (LDPE) have been found suitable for the storage and shipping of biological bulks at ambient or cold temperature (2 to 8° C.). However, problems exist in freezing applications with bags as currently configured. At low temperatures, the physical properties of plastic materials may change sufficiently to introduce brittleness that can reduce the capacity of the bag to absorb external forces, i.e., shocks without fracturing. In addition, ice volumetric expansion can cause significant mechanical stress leading to bag, port, tubing, or connector breakage. It is well known that current commercially available unprotected bags do not adequately protect frozen products.

To eliminate problems related to bag breakage, Sartorius Stedim Biotech has developed the Celsius™ FFT concept (FFT for "Flexible Freeze and Thaw"), which combines a flexible pouch with a semi-rigid protective shell. The contribution of the protective shell is predominant in the absorption of stresses resulting from processing or handling conditions.

Document US 2018/125757 provides a protecting body, so that the flexible pouch is sandwiched by the two plates of the protecting body, with a constraining effect. A freeze/thaw protection system may be obtained, by combining a single-use flexible container wrapped by such a protecting body and a protective shell. However, uniform fluid distribution may be difficult because, in a filled state of the flexible container, a significant bulge (big belly) in the middle is formed. In frozen state, ice expansion is thus relatively significant, and more time will be needed to freeze this big mass in the middle of the interior volume of the pouch.

Document WO 2015/200218 discloses a combination of single-use container (flexible container) and shell, in which a tufting coupling is provided, in order to divide the cavity of the container into a plurality of regions. This is of interest to limit risk of having a significant bulge, so that liquid mass concentration is prevented in a middle part of the flexible container. Such design cannot be widely used, especially because the container design is more complex, which increases the cost of the single-use container.

SUMMARY OF THE INVENTION

The purpose of the present invention is to provide a storage unit for obtaining a robust freeze/thaw containment and protection system efficient for conditioning a large amount of biopharmaceutical material in a flexible pouch (typically a 2D-pouch than inflates in a filled state) of flexible design, while keeping flexibility of design for the flexible pouch.

Besides, it would be of interest to have a storage unit suitable for efficient adaptation to various states of the pouch (non-filled state, filled state with more than 50 or 70 liters for instance) and various temperatures (causing significant differences in volume of the pouch when frozen).

To this end, embodiments of the present invention provide a system for conditioning a biopharmaceutical composition, for use in freezing, storing and thawing the biopharmaceutical composition contained in a flexible pouch, the system comprising:

a protecting body comprising two plates for protecting the pouch, the protecting body comprising a longitudinal axis and four sides, the four sides comprising two longitudinal sides extending parallel to the longitudinal axis and two other sides, an attachment system for fastening the two plates, the protecting body comprising a peripheral margin that extends annularly in a protecting body reference plane, the peripheral margin being provided with at least one opening able to receive at least one port of the pouch, a plurality of positioning members that are secured to or formed on the peripheral margin, and a frame extending around a hollow space, in which the pouch extends, and being provided with two longitudinal supporting parts that are separate from the positioning members, wherein the frame comprises abutment surfaces included and distributed in the two longitudinal supporting parts, the plurality of positioning members connecting the peripheral margin to the frame so that the frame retains and supports:

the protecting body; and the pouch that is sandwiched between the two plates which constrain the pouch, wherein sliders, forming positioning members of the plurality of positioning members, are slidably mounted on or in the two longitudinal supporting parts, in order to be movable along a direction transverse to the longitudinal axis, between:

a first position, in a non-filled-state of the pouch, in which the sliders are pushed outwardly or maintained away from the abutment surfaces by the protecting body, so that the sliders can be displaced inwardly (due to a change of conformation of the protecting body), and a second position, in a filled-state of the pouch, in which the sliders are each engaged against one of the abutment surfaces.

With such arrangement, it is possible to allow shrinkage (in/along the protecting body reference plane) of the protecting body due to the filling operation, with increase in height of the pouch, while possibly controlling shrinkage of the protecting body thanks to a control of the strokes of the sliders mounted at the peripheral margin. The protecting body may include two pieces (forming the plates) to constrain the pouch that is essentially made of two plastic sheets. The system can comprise a flexible pouch that is initially flat (in non-filled state) and configured to contain the biopharmaceutical composition in an expanded state of the pouch.

Filling the pouch causes a conformation change of the protecting body with shrinking of the protecting body in the protecting body reference plane, such shrinking of the protecting body resulting from the sliders passing from the first position to the second position. In empty state or low filled state (less than 5% or less than 1 or 2 kg for instance), relative rigidity of the protecting body is sufficient to have the gravity center of the mass of fluid (if homogeneous fluid) substantially placed in the reference plane. Typically, deformation of the lower plate may be similar or identical to deformation of the upper plate. At high filling levels, it is understood that the lower plate may be deformed downwardly with substantially same amplitude as the upper plate is deformed upwardly.

During filing operation, the sliders may be progressively displaced inwardly toward the abutment surfaces. The sliders are configured to allow a controlled shrinkage of the protecting body outer circumference in the protecting body reference plane.

The freeze/thaw containment system allows the peripheral margin to be mounted in a stationary frame, thanks to the sliding positioning members (sliders), which are typically secured to the peripheral margin, so that the peripheral margin is guided and allowed to be displaced inwardly during filling of the pouch. Such displacement occurs, while the protecting body extends generally planar to sandwich and constrain the pouch in empty state and low-filled state of the pouch. This way of holding and retaining the protecting body allows for progressive conformational change of the protecting body due to the change in volume of the pouch, while facilitating reverse displacement of the peripheral margin during draining operations. The constraining effect near the peripheral margin may be progressively and slightly released by displacement of the sliders, thus improving the filling near the pouch edges. Such arrangement is also compatible with a shrink management, for instance by controlling the sliding strokes of the sliders. This is of interest to have the protecting body remaining as flat as possible, for instance to keep a maximal height/thickness of the covering portion of the protecting body less than 24 or 25 cm, before or after the frozen state, when the pouch is large and adapted to be filled with at least 70 or 75 liters of biopharmaceutical composition.

Typically, the two longitudinal supporting parts are rigid, for example made of aluminum pieces or alloy pieces. More generally, density of the longitudinal parts may be much higher than 1, for instance superior to 2 $g/cm^3$. Besides, the tensile strength of the material of the longitudinal supporting parts may be about 120 MPa or more.

The Young module of the material of the longitudinal supporting parts is optionally comprised between 60 and 80 GPa. More generally, it is understood that the Young module of the longitudinal supporting parts is such that these parts are more rigid than the plates of the protecting body, which are in turn more rigid than the material forming the two sheets of the pouch.

Aluminum is well suited to cold environments. Optionally, inward deflection of the longitudinal parts (as measured perpendicular to the longitudinal axis) cannot exceed 5 mm for a longitudinal supporting part made of a piece that is more than 1200 mm long, so that these longitudinal parts are clearly rigid (very limited deflection).

The storage unit formed by the protecting body and the filled pouch can shrink in a controlled manner, through the sliders (acting for instance as stoppers) and the rigid parts, which may form a C-shape section frame or any similar section opened on interior side. Since the stoppers formed by the sliders are attached to the edges, in the peripheral margin, they may easily be encapsulated into respective housings delimited by the longitudinal supporting parts. A C-Shape frame may be of interest, in particular for adding a gap between the stoppers and the abutment surface, in order to allow the sliders/stoppers to move.

Typically, the protecting body may have a peripheral side of rectangular shape (i.e. with two parallel long sides and two short sides perpendicular to the long sides). Moreover, the system may be provided with sliders that move in one direction:

which defines a X-direction for the sliders/stoppers located on the long side of the protecting body;

which defines a Y-direction for the sliders/stoppers located on the short side of the protecting body;

where X corresponds to direction of the longitudinal axis $X1$ and Y corresponds to a transverse direction, these directions being along the protecting body reference plane.

This two axis freedom of motions will allow to the protecting body to shrink and to expend vertically (i.e. along Z-direction, in order to fill the pouch at the required volume, without allowing too great shrinkage in some middle regions). Such control effect may be also obtained, with efficiency in limiting the maximal height of the protecting body and limiting bulge effects, by using sliders only located on the long sides of the protecting body, in the peripheral margin.

It is understood that the two plates are flexible enough to allow the protecting body to have a thickness in a central area greater than in a circumferential area, in reference to the protection body reference plane, the thickness being measured between the lower surface and the upper surface along a direction perpendicular to the protection body reference plane.

According to an embodiment, the flexible pouch is directly sandwiched between the two plates which constrain the flexible pouch. The flexible pouch is typically more flexible than material of the protecting body. The constraining effect is of interest for a step of emptying the flexible pouch, and is advantageous to limit expansion of the fluid (vertical expansion when the protecting body extends generally horizontal so that the protecting body reference plane extends substantially horizontal), especially during freezing.

The two plates may constrain the flexible pouch by a respective covering portion that extends between two margin portions of the peripheral margin.

Typically, the protecting body is mounted to cover the two main opposite faces of the flexible pouch, and acts as an expansion guiding element adapted to deploy in volume in an expanded state, so that the assembly composed of the protecting body and the flexible pouch covered by the protecting body can fill an inner cavity delimited by or an interspace delimited between the two protecting parts, without bulging too much in a covering portion middle part provided at equal distance from front and rear edges of the flexible pouch and separating two other complementary parts of same longitudinal size as a determined longitudinal size of the middle part (the determined size thus being substantially equal to one third of the longitudinal size of the flexible pouch as the covering portion has same length as the flexible pouch).

The plates are removably fixed to each other by the attachment system, which is distributed (selectively) in the peripheral margin.

Two opposite margin portions, provided longitudinally in the peripheral margin, are part of a fastening assembly to prevent any shifting in position between the two plates once they are mutually fastened at least in the two margin portions, in a predetermined superimposed configuration for forming the protecting body.

In the two opposite margin portions, protruding parts of the plates are provided, the protruding parts protruding in a single direction or in two opposite directions. The protruding parts may form first interlocking elements engaged, snap-fastened, fitted or loosely fitted/received in cavities of the positioning members. Additionally or alternatively, tongues may be provided in the positioning members, the tongues being inserted in hollows of the margin portions, such hollows being typically delimited internally by the protruding parts (which are hollow protruding parts).

One or more tongues and one or more cavities of the positioning members may be formed in a same piece that is either a lower part arranged below the peripheral margin of the protecting body (below the reference plane), or an upper part arranged above the peripheral margin of the protecting body (above the reference plane).

Optionally, each of the two plates comprises embossments or boss portions, which define, in assembled state of the plates (to form the protecting body), several protecting body embossments protruding in a first direction perpendicular to the protecting body reference plane. They may be hollow, in order to form corresponding cavities opening in a second direction opposite to the first direction. Such embossments or boss portions are selectively distributed in the peripheral margin.

Two groups of boss portions may be provided, with boss portions of the first group protruding in the first direction, while boss portions of the second group are protruding in the second direction.

The positioning members may be provided with one or two recesses configured for insertion, preferably fitted insertion or clipping, of boss portions of the plates. The positioning members may also be provided with tongues for fitted insertion or clipping in hollows or cavities of the peripheral margin.

Typically, the positioning members are fixed by a plugging action, by a simple pushing along a direction transverse to the protecting body reference plane. Such plugging may be performed before or after assembling the two plates together.

Alternatively, several protecting body through-slots are provided and longitudinally distributed in each of the two opposite margin portions.

The attachment device may interact with some of the protecting body through-slots or may be distributed in alternate locations relative to the protecting body through-slots.

Typically, the frame intersects the protecting body reference plane and extends parallel to the protecting body reference plane, the frame being configured to hold the protecting body, directly or indirectly.

In variants, one of the four sides is suppressed so that the frame comprises three profiles extending parallel to the protecting body reference plane.

According to particular feature, at least one of the two plates is provided with ribs protruding outwardly to locally structure the protecting body, at least in peripheral regions around a middle part of the protecting body. The plates may be each provided with one or two panel parts without any ribs, externally delimited by ribs having a U-shaped design as observed in elevated view (away from the protecting body reference plane).

In various embodiments of the system, recourse may optionally also be had to one or more of the following dispositions:
- the two plates are two pieces (distinct pieces) having each four edges, each piece having a planar inner face (each planar inner face entirely covering one of the two outer faces of the pouch in non-filled state).
- the two plates may have a same thickness that is lower than 2 mm, each of the two plates having a density superior to 1.10 g/cm$^3$ and being made of plastic material.
- the two plates are made of same plastic material, preferably transparent or translucent
- the protecting body is made of a freeze resistant polyester or copolyester material that is not brittle at about 25° F. or −4° C.
- the material of the protecting body is PET.
- the material of the protecting body is TRITAN (i.e. a copolyester compound called TRITAN™, which is a transparent amorphous thermoplastic material, typically made by combining three monomers; some formulations of this material do not contain additives, while others contain about or less than 10% additives).
- the material of the protecting body is an amorphous copolyester made by combining the following monomers: dimethyl terephthalate, 2,2,4,4-tetramethyl-1,3-cyclobutanediol, and 1,4-cyclohexanedimethanol.
- the protecting body is directly engaged by positioning members that belong to the attachment device, in order to have a profile of shrink at the protecting body circumference, optionally with almost no reduction or less shrink due to direct engagements of the positioning members engaged in a middle region of the protecting body, at the margin portions.
- the positioning members are distributed around the covering portion.

each of the positioning members is engaged to extend through one of the two opposite margin portions, by extending through at least one cut or recess formed in one of the two margin portions.

the protecting body reference plane intersects four margin portions distributed in a rectangular shape and each in contact with the two protecting parts of the shell, the four margin portions being arranged around the covering portion, the two opposite margin portions being part of this group of four margin portions.

the positioning members, which are distinct and separate from the pouch and from the plates, are configured to protrude each from at least one amongst a lower surface and an upper surface of the protecting body, in the peripheral margin.

the protecting body extends planar in an empty state of the pouch, along the protecting body reference plane;

and wherein the two plates are flexible enough to allow the protecting body to have a thickness in a central area greater than in a circumferential area, in reference to the protection body reference plane, the thickness being measured between the lower surface and the upper surface of the protecting body along a direction perpendicular to the protection body reference plane;

the pouch is directly sandwiched between the two plates which constrain the pouch.

the positioning members are part of the attachment system.

the positioning members are provided with one or more plug parts, in order to be removably plugged on the peripheral margin.

the peripheral margin is of rectangular shape and is provided with a plurality of hollows, distributed in the two longitudinal margin portions, which are the two longer portions of the peripheral margin.

the plurality of hollows includes at least one hollow in one or two shorter margin portions of the peripheral margin, each shorter margin portion being elongated along a transverse direction.

each of the positioning members is filling (and covering) at least one of the hollows provided in the peripheral margin.

at least one of the positioning members is overlapping a part of the attachment system.

optionally, the positioning members do not extend beyond an outer circumference (defining the outer perimeter) of the protecting body.

the positioning members comprise each a lower part and an upper part that are two separate pieces configured to sandwich the protecting body, in a region of the peripheral margin.

the positioning members comprise each a lower part and an upper part that are two separate pieces configured to sandwich the protecting body, in a sandwiching region of the peripheral margin, each sandwiching region being elongated, parallel to a protecting body edge, and preferably at least four times longer than a maximal width of the positioning members.

the sliders are part of the attachment system.

the sliders support or include each an insert piece engaged in the protecting body through thickness of the peripheral margin.

the positioning members are distributed at different longitudinal locations along the longitudinal axis.

the two longitudinal supporting parts may cover or overlap two opposite margin portions of the peripheral margin.

the peripheral margin may be received in four respective housing of a frame structure, which includes the two longitudinal supporting parts.

the two longitudinal supporting parts are part of a holding and retaining device, typically constructed has a frame, the positioning members being each provided with two separate parts (upper and lower parts) that are interlocked, in order to have the protecting body sandwiched between the two separate parts and arranged in the interspace that is delimited by the two separate parts.

the frame comprises profiles, for instance with U-shape or C-shape section, each delimiting an internal cavity, the positioning members being each arranged inside one of the respective cavities of the frame, in order to have the positioning members selectively movable inwardly according to a stroke that depends on an interspace provided inside a cavity, the positing members acting as stoppers for limiting expansion of the protecting body when an abutment surface that belongs to a given positioning member abuts against an abutment edge or abutment surface included in the profile (which is housing the given positioning member).

the abutment surfaces are included in abutment members which extend transversely relative to the protecting body reference plane (abutment surfaces cooperating with sliders movable along transverse direction).

each of the abutment members is configured to separate the hollow space from a cavity where at least one of the sliders extend.

The abutment surfaces may be formed after forming the storage unit, which comprises or consist in the pouch, the protecting body, the attachment system with the positioning members.

Once the positioning members are coupled to the peripheral margin, the sliders can be encapsulated (with the protecting body edges, the whole peripheral margin being typically concerned) into C-Shaped profiles of the frame structure/frame or in any suitable housing of the frame. The two longitudinal parts may form two profiles of the frame.

This encapsulation allows the protecting body to be better maintained, selectively at the peripheral margin, with the pouch safely protected. In addition, the encapsulation will allow managing the changes of conformation of the storage unit as desired during filling operations and changes of temperature (with freezing operation).

It is understood that filling of the pouch with the biopharmaceutical composition causes expansion along a direction perpendicular to the protecting body reference plane, which means shrinkage of the protecting body (in the protecting body reference plane) until reaching an abutment configuration (second position for the sliders).

In some embodiments, the abutment surfaces may be formed as any suitable stopping parts distributed in the two longitudinal slides/profiles/supporting parts and they are configured to stop the sliders by abutment of a front abutment surface included or supported by the sliders.

A first longitudinal supporting part chosen amongst the two longitudinal supporting parts may define a first housing, the sliders comprising first sliders fitted in at least one cavity delimited by the first housing.

Additionally, the two longitudinal supporting parts may comprise a second longitudinal supporting part that defines a second housing, the sliders also comprising second sliders fitted in at least one cavity delimited by the second housing.

In some options, the sliders include an elongated piece of molded plastic material, having a first long side and a second long side which are substantially parallel (and parallel to a protecting body side when coupled to a margin portion). The sliders, which may have a rectangular shape, have interlocking means or plug parts, arranged closer from the first side than from the second side, the sliders being coupled to the protecting body by the interlocking means or plug parts. Typically, the second side forms an offset contact face for early contact with the abutment surface when the second side is facing the abutment surface.

Orientation of the elongated pieces is such that the positioning members (typically arranged in profile cavities or similar cavities of the frame) are more or less close to the abutment surfaces in the initial non-filled state of the flexible pouch. The positioning members having the second side facing the abutment surfaces will be early stopped by the abutment surfaces during filling operation. In other words, same elongated pieces having such a dissymmetry may serve to form positioning members that can restrict more or less the shrinking of the plates, when mounted (and engaged) in/inside the longitudinal supporting parts belonging to the frame. Higher restriction of such shrinking is preferred at or near a median transverse plane of the protecting body (middle region). In some embodiments, the frame is further provided with one or two transverse supporting parts that are rigid and separate from the positioning members. Typically, each of the one or two transverse supporting parts is housing additional sliders that:
    form each a positioning member of the plurality of positioning members,
    are each slidably mounted on or in a corresponding transverse supporting part, in order to be movable along direction of the longitudinal axis.

The frame has a rectangular shape thanks to the two longitudinal supporting parts and the transverse supporting parts. The peripheral margin is also rectangular (corresponding to a rectangular peripheral side/perimeter). For compactness, the abutment surfaces may be provided in regions in an overlapped configuration relative to the peripheral margin. Such abutment surfaces thus do no extend radially beyond an outer perimeter of the protecting body.

The frame comprises additional abutment surfaces included and distributed in the two transverse supporting parts, the additional sliders being movable along direction of the longitudinal axis between:
    a first position, in a non-filled-state of the pouch, in which the additional sliders are pushed outwardly or maintained away from the additional abutment surfaces by the protecting body, so that the additional sliders can be displaced inwardly due to a conformation change of the protecting body,
    and a second position, in a filled-state of the pouch, in which the sliders are each engaged against one of the additional abutment surfaces.

The supporting parts belong to a holding and retaining assembly that allows the two plates moving, extending, and shrinking in a transverse direction belonging to the protecting body reference plane.

The protecting body has a rectangular shape with four corner regions away from a middle region of the protecting body, wherein at least four corner sliders, preferably at least six corner sliders, chosen amongst the sliders and the additional sliders are distributed at respective ends of the two longitudinal supporting parts and at respective ends of the two transverse supporting parts, in order to increase shrinking of the protecting body in the protecting body reference plane in each of the four corner regions during filling of the pouch.

In some options, the protecting body has a rectangular shape with four corner regions away from a middle region of the protecting body, and wherein the sliders comprise sliders, preferably four sliders, distributed at respective ends of the two longitudinal supporting parts, in order to increase shrinking of the protecting body in the protecting body reference plane in at least one of the four corner regions.

In some options, the system further comprises biasing members that are configured to exert a return action for displacing the sliders outwardly toward the first position which is a by-default-position in non-filled state and in an emptied state of the pouch.

During filling operations, filling of the pouch causes progressive deformation of the protecting body, in order to create in the protecting body reference plane a pulling action to pull the sliders inwardly, the pulling action increasing with level of filling of the pouch and being opposite to the biasing action of the return members.

The biasing members may include each one amongst a leaf spring, a compression spring and an extension spring.

In some options, the biasing members are return members provided with one or more magnetic members. A respective movable one of the magnetic members; so called a driving member, is fixed to or integral with the corresponding/associated slider, and is configured to be movable together with the associated slider.

All or part of the sliders are provided with contact parts in contact with the abutment surfaces in the second position, the contact parts being biasing members configured to exert a return action for displacing the sliders outwardly toward the first position which is a by-default-position in non-filled state and in an emptied state of the pouch.

The contact parts may be deformable between an inactive conformation, compatible with the first position of the sliders, and an active resiliently compressed conformation, in which the contact parts are in contact with the abutment surfaces. The active conformation is obtained in a filled-state of the pouch, due to shrink/displacement of the peripheral margin, inwardly in the protection body reference plane.

The contact parts may be porous parts, possibly including foam or alveolar material, which is resiliently compressible, the contact parts being in a compressed state in the second position.

In some options, the contact parts are pressing on the abutment surfaces both in the first position and in the second position, the contact parts belonging to leaf springs or similar springs that are more deformed/compressed (and thus energized to form the return members) in the second position.

The biasing members may be or form front parts of the sliders, in contact with the abutment surfaces.

The biasing members may be mechanically coupled to the sliders so that the sliders are biased or pushed outwardly (to return to a default position) by the biasing members toward the first position when the weight of the pouch with the biopharmaceutical composition contained therein is below a threshold.

In some embodiments, the protecting body is provided with positioning members that are interface elements between the peripheral margin and a frame structure. Such positioning members have compressible contact parts allowing a sliding, the contact parts being optionally of different size, as measured along radial direction. With such different in size, a group of middle region positioning members may be less compressed and locally limit the shrinking of the protecting body.

More generally, several positioning members or similar interface elements may be provided with deformable parts for contact against abutment surface of the rigid frame, the deformable parts being either in contact with the abutment surfaces or integrated in intermediates position between a contact end and the peripheral margin of the protecting body.

The plates may, directly or indirectly, support the deformable parts so that the deformable parts extend around the covering portion of the protecting body. Elastic return members or compressible members may be such deformable parts.

In some embodiments, the system comprises pull elements that are displaceable transversely relative to the two longitudinal supporting parts and coupled to portions of the peripheral margin. The pull elements may be configured to pull all or part of the peripheral margin outwardly when the pull elements are displaced from a retracted position to an expanded position. The pulling may be manually operated or performed through a driving member.

The pull elements may be loosely guided through respective windows or other guiding elements provided in a frame that includes the two longitudinal supporting parts.

Some embodiments of the invention also provide a method of assembling a system according to the invention, which is a protection system for storing and withstanding freezing and thawing of the biopharmaceutical composition contained in the pouch of the freeze/thaw containment system, the method comprising:
  sandwiching a flexible pouch between two plates of a protecting body, selectively by a covering portion distributed in the two plates for covering the flexible pouch, the protecting body being configured for protecting the flexible pouch and comprising the two plates, the protecting body further having a longitudinal axis and comprising four sides, the four sides comprising two longitudinal sides extending parallel to the longitudinal axis and two other sides;
  using an attachment device for fastening the two plates so that in an assembled state of the two plates, the protecting body comprises a peripheral margin that extends annularly in a protecting body reference plane, around the covering portion, the peripheral margin being provided with:
    at least one opening receiving at least one port of the flexible pouch, and
    a plurality of positioning members that are secured to or formed on the peripheral margin,
  wherein, in the assembled state of the two plates, a frame is mounted around the protecting body, by coupling two longitudinal supporting parts that are separate from the positioning members to the peripheral margin, the two longitudinal supporting parts extending parallel to the longitudinal axis when coupled to the peripheral margin, in order to form two opposite sides of the frame, the plurality of positioning members connecting the peripheral margin to the frame,
  wherein abutment surfaces are included and distributed in the two longitudinal supporting parts, so that the frame retains and supports:
    the protecting body; and
    the pouch that is sandwiched between the two plates which constrain the pouch, and wherein sliders, forming positioning members of the plurality of positioning members, are slidably mounted on or in the two longitudinal supporting parts during mounting of the frame, in order to be movable along a direction transverse to the longitudinal axis, between:
      a first position, in a non-filled-state of the pouch, in which the sliders are pushed outwardly or maintained away from the abutment surfaces by the protecting body,
      and a second position, in a filled-state of the pouch, in which the sliders are each engaged against one of the abutment surfaces.

With such method, an efficient storage unit, forming a cassette, is obtained with a planar configuration before mounting the frame. For flexible pouches of high capacity, superior to 50 or 70 liters, this is of interest as the frame can be made of demountable side members, which can be stored in a reduced space in disassembled state.

For instance, assembling of the frame may be performed using the following steps:
  assembling one side or two parallel sides, preferably the short sides (which may have each a C-shaped section or any suitable section for a retaining action), by sliding them on or around the corresponding margin areas of the storage unit provided with the positioning members (so that the one or two frame sides are arranged below the protecting body at the peripheral margin); and
  assembling two other sides, preferably the long sides (which may also have a C-shaped section or any suitable section for a retaining action), by sliding them on or around the corresponding margin areas of the storage unit (so that the two frame sides are arranged below the protecting body at the peripheral margin), so that a frame extending along the protecting body reference plane is obtained.

With such frame structure, assembling and disassembling may be performed quickly. A stacking of several systems may be obtained, feet forming vertical spacers between the frames being possibly added and fastened (with a possible additional step for forming the system, by fastening four feet in the corners of the frame).

Other features and advantages of the invention will become apparent to those skilled in the art during the description which will follow, given by way of a non-limiting example, with reference to the appended drawings.

BRIEF DESCRIPTION OF THE DRAWINGS

FIG. 10 illustrates stacked systems such as shown in FIG. 4, respectively before filling of the pouches and in a filling state of the pouch, in order to show the pouches remain relatively flat and can still expand due to freezing of their content;

DETAILED DESCRIPTION OF EMBODIMENTS

In the various figures, the same references are used to designate identical or similar elements.

In the different Figures, a vertical direction, a longitudinal direction and a lateral direction are based on the freeze/thaw containment system horizontally stored in a shelf. A direction perpendicular to the longitudinal direction is the lateral direction. One direction according to the height of the freeze/thaw containment system 1 is the vertical direction, reflected by direction Z in the FIG. 4A in particular.

Figure 4A:
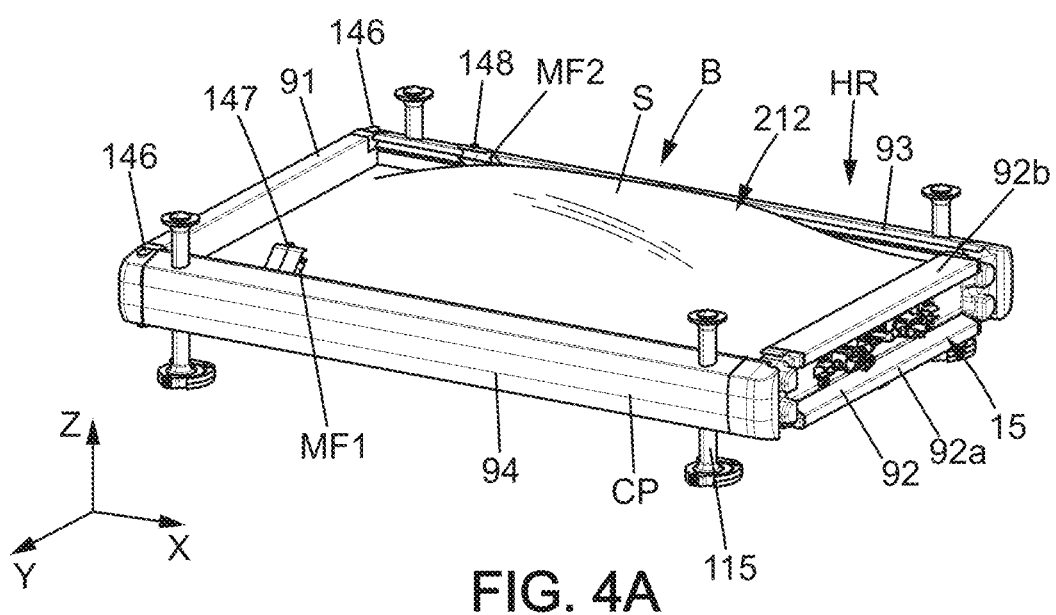
FIG. 4A is a perspective view showing a freeze/thaw system, using a peripheral frame that houses internal positioning members, in a filled configuration in which the positioning members are not active to limit inwardly movement and shrinking of the plates that sandwich the flexible pouch.
Figure 6A:
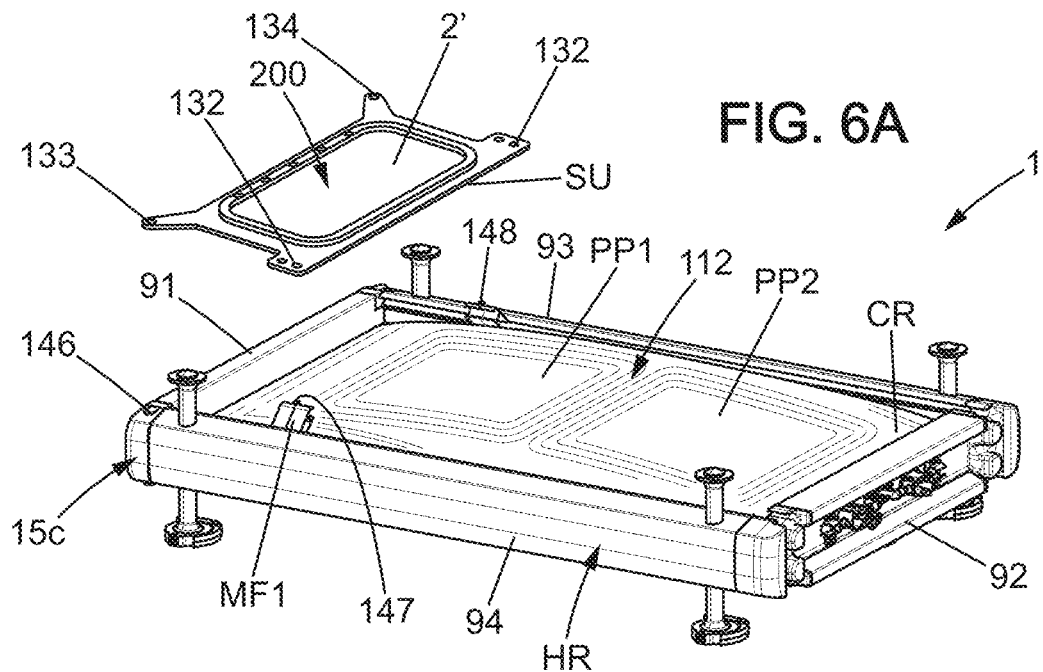
FIG. 6A is a perspective view of a freeze/thaw containment system able to support and attach a sample unit, here with some of the internal positioning members adjusted to selectively limit plate displacement and shrinking in a middle region of the protecting body, the plates being provided with a ribbing pattern.

In embodiments of the invention, the freeze/thaw containment system 1 may be such as illustrated in FIGS. 4A and 6A, in order to include a protecting body (12, 112, 212) that covers both faces of a flexible pouch 2 for biopharmaceutical materials, hereafter called biopharmaceutical composition Q.

Referring to FIG. 1-2A or 3, the protecting body 12 or 112 comprises two plates 12A, 12B for protecting the flexible pouch 2. The two plates 12A and 12B may be made separate. The protecting body 12 or 112 comprises ribs, typically on each plate 12A, 12B, while the protecting body shown in FIG. 4A comprises at least one outer surface S without any ribs.

The protecting body 12, 112, 212 is obtained by fastening the two plates 12A, 12B in a circumferential part that surrounds a covering portion 8 that belongs to the protecting body 12. For instance, the protecting body 12, 112, 212 is assembled when sandwiching the empty pouch 2 by the covering part, by securing the circumferential parts of the plates 12A and 12B together. For this, an attachment device or attachment system 18 is provided, in order to fasten the two plates 12A, 12B. In an assembled state of the two plates 12A, 12B, the protecting body 12, 112, 212 comprises a peripheral margin 80. The peripheral margin 80 is obtained by securing respective margin portions 8a, 8b of the plates. Each plate annular margin may be composed of four outer band regions of the plates 12A and 12B.

The protecting body 12, 112, 212, provided with or without ribs, extends planar, along a protecting body reference plane P, and cannot inflate like a thin rubber balloon, as the plates 12A, 12B are relatively rigid to constrain the pouch 2. The protecting body 12, 112, 212 is typically as rigid as or more rigid than a PET bottle for containing sparkling water, thus allowing very limited deformation as compared to the material of the flexible pouch 2.

The freeze/thaw containment system 1 is provided with several positioning members PM that are secured to or formed on this peripheral margin 80. This peripheral margin 80 may be seen as the part of the protecting body which is complementary to a covering portion 8 where the pouch conformation changes, depending on the level of filling of the pouch 2. The system 1 also comprises a frame 15 that is constructed to surround a hollow space where the pouch 2 extends. The frame 15 may be provided with two longitudinal supporting parts 31 that are constructed to be distinct/separate from the positioning members PM.

Referring to FIGS. 4B-4G, 5A-5B, 6A-6D, 7A-7B and 8, the positioning members PM, PM' may be parts of the attachment system 18 and/or may participate to sandwich the two plates 12A, 12B of the protecting body, at the peripheral margin 80. The positioning members PM, PM' may be composed of at least two pieces, which are distinct and separate from the pouch 2 and from the plates 12A, 12B. Here, they comprise several pairs of flat bars UP, LP or UP', LP', possibly pinching the plates 12A, 12B when using an insert protrusion IP1, IP' integrally formed with the bar or an insert piece IP such as a screwing element (such screwing elements being provided separate from the protecting body). Typically, the bars UP, LP or UP', LP' are grouped in respective pairs for assembling the flat bars above and below a same region of the peripheral margin 80, thus forming the positioning member PM, PM'. More generally, the positioning members PM, PM' may be rigid parts, typically made of plastic material (for instance HDPE), provided with fastening pieces or integrated fastening means.

Figure 4B:
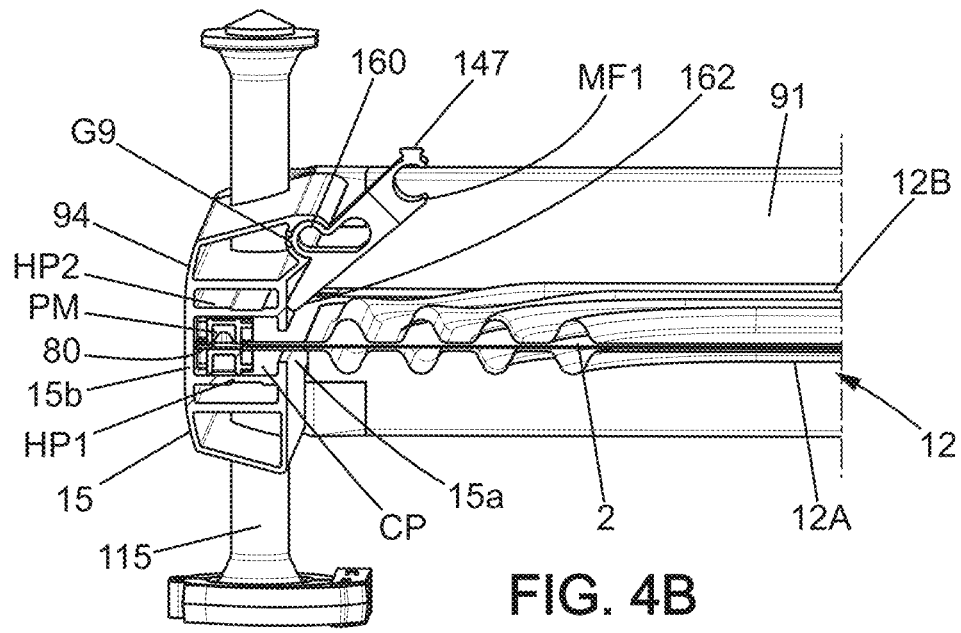
FIG. 4B is a vertical cut view illustrating an exemplary integration, inside a frame profile, of a positioning member formed as a slider that is movable inwardly relative to a stationary frame part.
Figure 11A:
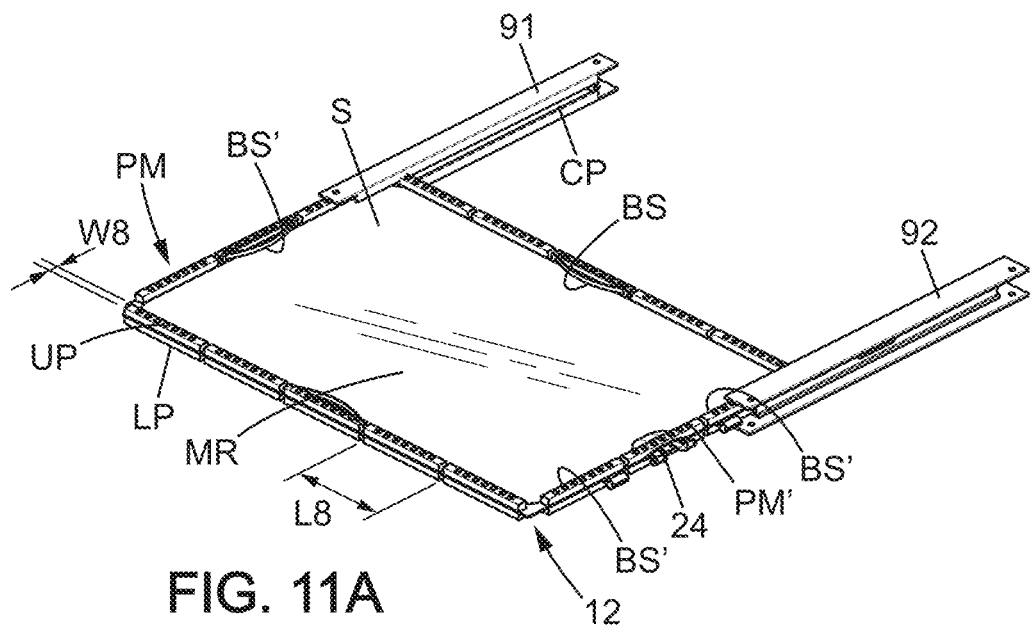
FIGS. 11A, 11B, 11O show respective steps performed when forming a frame for handling and storing a storage unit including the positioning members, with an optional step of fastening feet to define a stackable shelf module.

The positioning members PM, PM' are configured to protrude each from at least one amongst a lower surface S' and an upper surface S of the protecting body 12, 112, 212, in the peripheral margin 80. Typically, the positioning members PM comprise each a lower part LP and an upper part UP that are two separate flat bars or any suitable pair of pieces configured to sandwich the protecting body, in a region of the peripheral margin 80, outside the hollow space of the frame where the pouch 2 extends. The lower and upper parts may be identical pieces forming the bars, as in the non-limiting embodiment of FIGS. 4C, 4D and 4F. Each pair of bars LP, UP forms a positioning member PM that can be housed or engaged in the frame, as described below. An additional positioning member PM', different from the other positioning members PM, is illustrated in FIG. 4E-4F, allowing ports 24 to extend horizontally through the positioning member PM'. More generally, a specific positioning member PM' can sandwich a part of the peripheral margin 80 where the at least one port 24 extends, as shown in FIGS. 4G, 11A. In some variants, the positioning members can only include members PM away from the port(s) 24 or without any specific member extending around the port(s) 24.

Referring to FIGS. 4E-4F, the upper and lower parts LP' and UP' of the positioning member PM' may be mounted after attaching the plates 12A, 12B together. The same may apply for the positioning members PM.

The insert protrusions IP' of each of the parts LP' and UP' are distributed away from the connector parts of the ports 24, here away from a central opening OPC that is disposed between two openings OP1 and OP2 for passage of two ports 24. Another port may extend through the central opening OPC. In the positioning members PM and PM', insert protrusions IP1, IP' may act as interlocking members or plug parts cooperating with corresponding reliefs formed in the peripheral margin 80.

It can be seen that the positioning member PM, PM' extend typically only around the covering portion of the protecting body 12, 112 or 212.

Figure 6B:
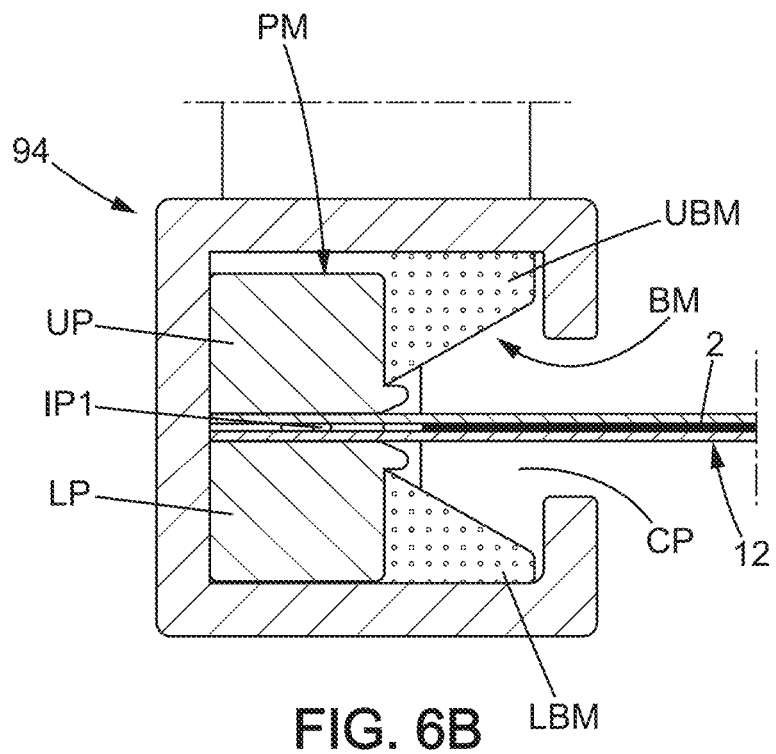
FIG. 6B is a vertical section view of a detail of the system, showing an optional biasing member provided at interface between an abutment surface of the frame and a sliding positioning member secured to a peripheral margin part of the protecting body.
Figure 6C:
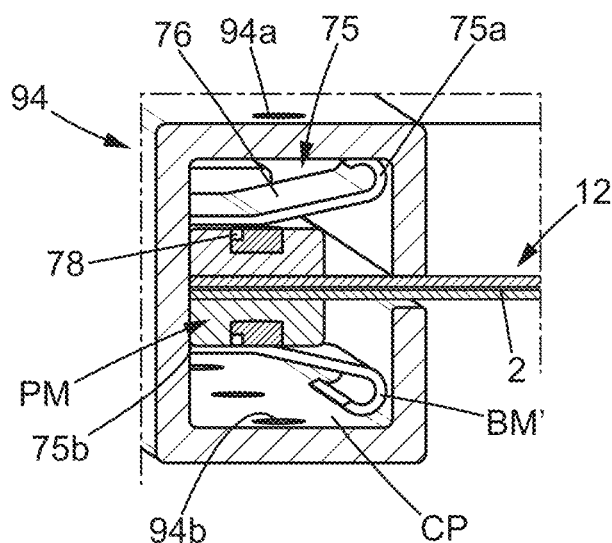
FIG. 6C is a side view of another optional biasing member member provided at interface between an abutment surface of the frame and a sliding positioning member secured to a peripheral margin part of the protecting body.
Figure 6D:
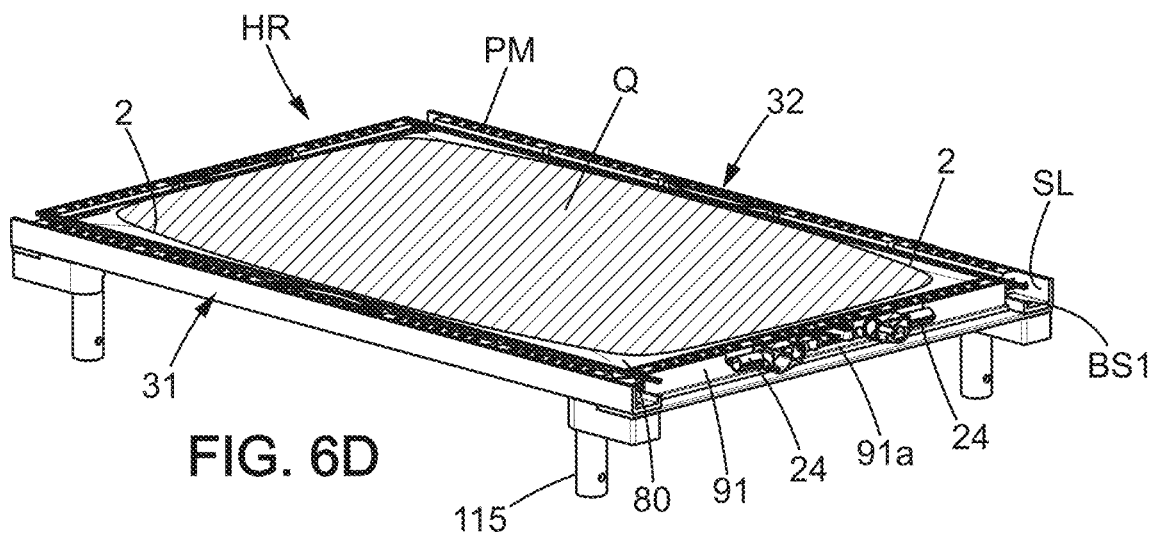
FIG. 6D illustrates an exemplary distribution of positioning members around the protecting body, when using a frame identical or similar as the one shown in FIG. 6A.

In the system shown in FIG. 6A or 6D, it is understood that a storage unit 10 can be obtained with the protecting body 112 unable to be detached from the frame 15, due to a fastening provided for holding and maintaining the positioning members PM, PM' relative to the respective parts or profiles 91, 92, 93, 94 of the frame 15. Here, the fastening is adapted to allow the protecting body to move, extend, and shrink along the protecting body reference plane P, i.e. providing a degree of freedom along at least one amongst the directions of axes X and Y shown in FIGS. 1 and 4A.

When the positioning members PM, PM' are part of the attachment system 18, the attachment system 18 can be considered as an assembly of several displaceable parts that can move inwardly relative to the frame 15. Here, the frame 15 comprise two elongated longitudinal supporting parts formed by two pieces or profiles 93, 94, that define each a housing for accommodating respective positioning members PM. At least one of the positioning members PM constitutes a slider movable inwardly inside the corresponding housing.

Referring to FIGS. 3, 4B-4G, 6B-6C, 7A-7B, 8 and 11A, it can be seen exemplary embodiments, in which each lower part LP and an upper part UP are two separate pieces configured to sandwich the protecting body, in a sandwiching region of the peripheral margin 80. Each sandwiching region may be elongated, parallel to a protecting body edge, by extending longitudinally to be at least four times longer (with a length L8) than a maximal width W8 of the positioning members PM, as illustrated in non-limiting embodiment of FIG. 11A in particular.

Referring to FIGS. 4A, 5A-5B and 7A-7B, all or part of the frame 15 forms a holding and retaining assembly HR. This assembly HR has abutment surfaces AB1, AB2, here provided in the two profiles 93, 94 that are exemplary pieces forming longitudinal supporting parts for supporting the protecting body provided with the fastening system 18.

More generally, it is understood that the frame 15 typically comprises abutment surfaces AB1, AB2 included and distributed in the two longitudinal supporting parts, all or part of the positioning members PM connecting the peripheral margin 80 to the frame 15 so that the frame 15 retains and supports:

the protecting body 12, 112, 212; and
the pouch 2 that is sandwiched between the two plates 12A, 12B.

Some or all of the positioning members PM constitute sliders, which are slidably mounted on or in the two longitudinal supporting parts, in order to be movable along a direction transverse to the longitudinal axis X1 (axis of the protecting body, which may be merged with longitudinal axis A of the pouch 2), between:

a first position, in a non-filled-state of the pouch 2, in which the sliders are pushed outwardly or maintained away from the abutment surfaces AB1, AB2 by the protecting body 12, 112, 212 (when having its flat rectangular shape with a maximal perimeter), so that the sliders are able to be further displaced inwardly, and a second position, in a filled-state of the pouch 2, in which the sliders are each engaged against one of the abutment surfaces AB1, AB2.

In some options, positioning members PM may form guiding parts for receiving one or more body crossing members. Referring to FIG. 5B, holes 18o may be provided in the positioning members PM for introducing rod-like crossing members cooperating with a locking part, a nut or bolt. Of course, slots may be provided in the protecting body 12, 112 or 212, for allowing the body crossing members to cross the peripheral margin 80 at a plurality of locations. However, in preferred options, as illustrated in FIGS. 2B and 4B-4F in particular, the positioning members PM, PM' may simply sandwich, with discontinuous distribution, the peripheral margin 80, while being unable to be disassembled once they are introduced in the frame 15 (in any elongated cavity CP of the frame 15), typically inside profiles 91, 92, 93, 94. Thus, there is no need for any additional insertion piece IP and the margin portions 8a, 8b may be provided with embossments or boss portions B12, B12' for engagement with corresponding reliefs (cavities CF1) of the positioning members PM, PM.

Figure 2A:
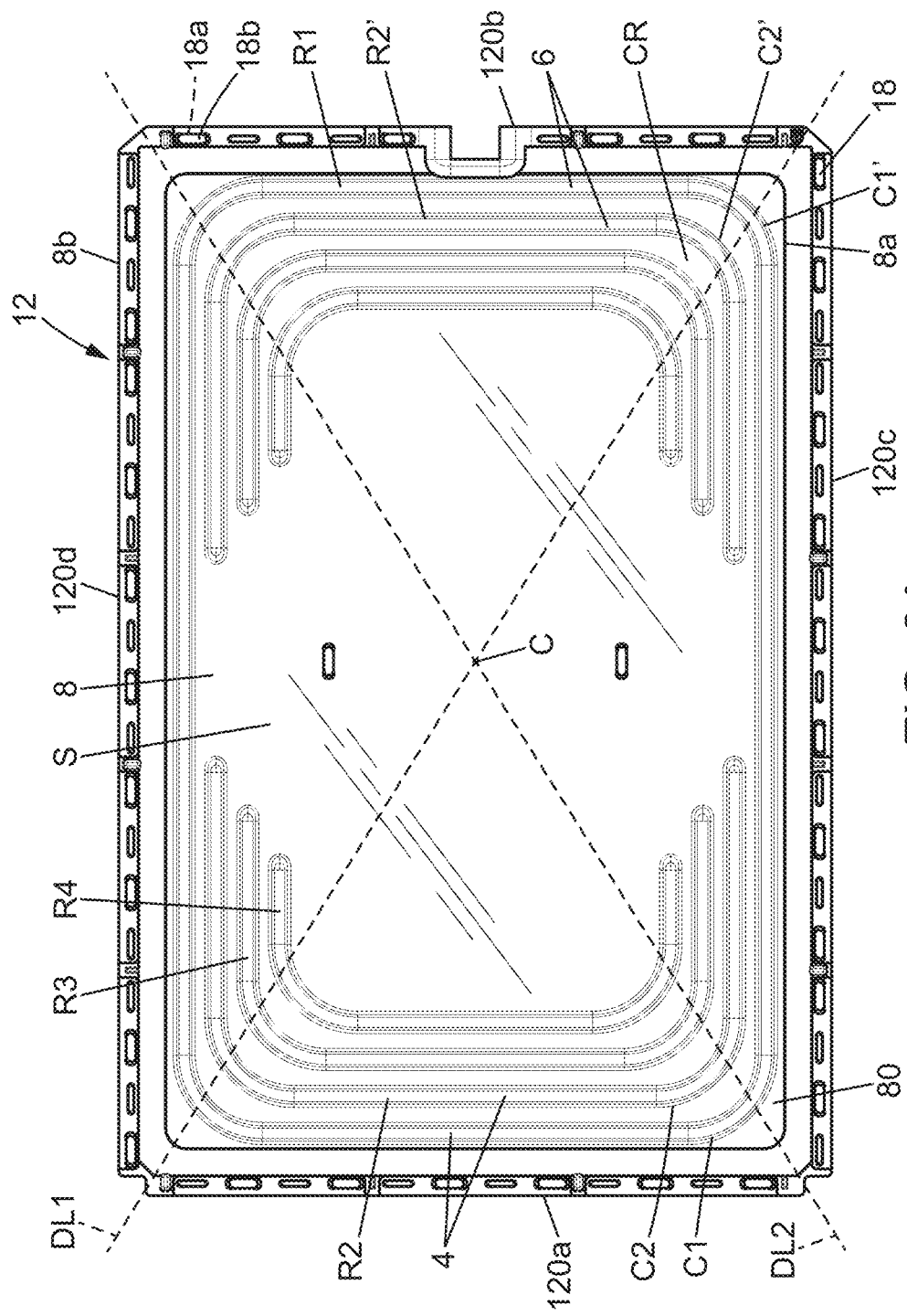
FIG. 2A is a top view showing the storage unit of FIG. 1 assembled, with a ribbing pattern provided on the protecting body top surface, including fastening members for affixing a bag, directly or indirectly.
Figure 2B:
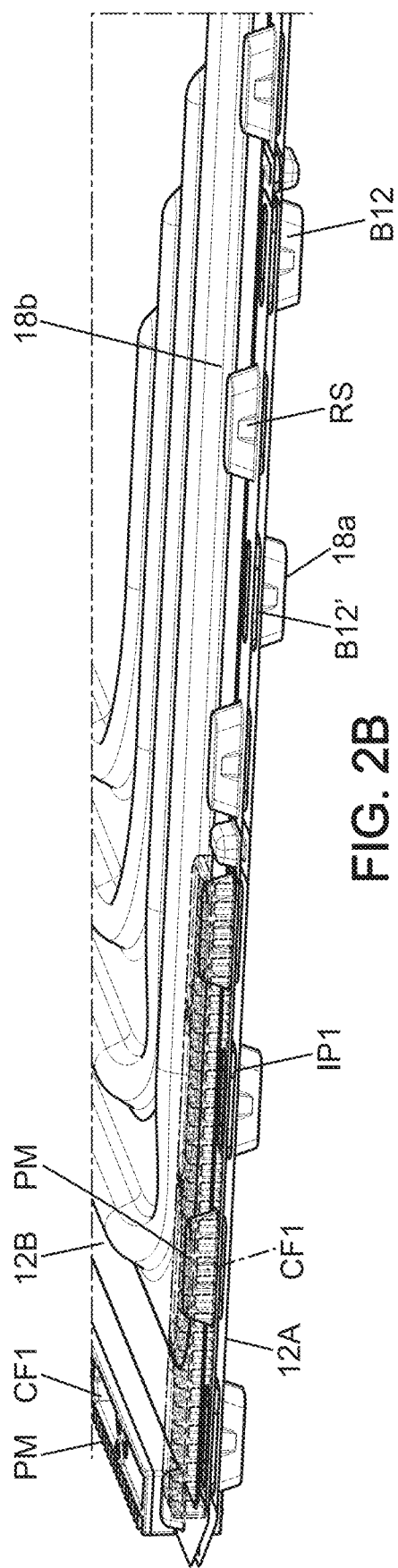
FIG. 2B is a side view illustrating an exemplary interlocking between the two plates, and showing a positioning member according to a preferred embodiment, in which the positioning member is coupled to the protecting body at a peripheral margin by interlocking forms.
Figure 3:
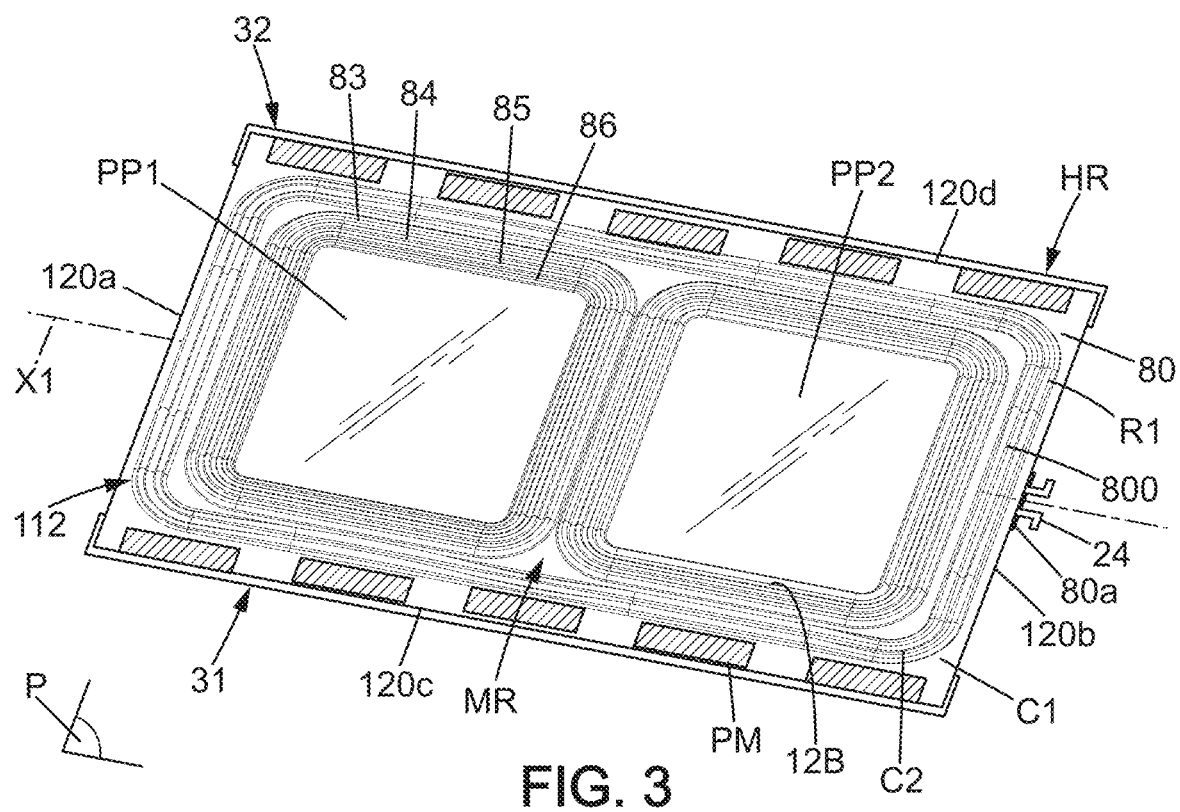
FIG. 3 illustrates a freeze/thaw containment system, in which a flexible pouch is sandwiched between the two plates forming the protecting body, in an empty state of the pouch, while a peripheral margin of the protecting body is sandwiched between positioning members.

Referring to FIGS. 2-3, the peripheral margin 80 may extend annularly in a protecting body reference plane P, the peripheral margin 80 being provided with at least one opening 80a able to receive at least one port 24 of the flexible pouch 2. Two front ports 24 may be provided. The openings or ports may be formed as closable tubes for example, and may be provided between facing parts of a welded joint where two constitutive sheets of the pouch are joined. Such openings may be of interest, to allow the pouch to be filled or emptied. For example, one port forms an inlet for the flexible pouch 2 and the other port forms an outlet of the flexible pouch 2.

The protecting body 12, 112, 212 may extend planar along the protecting body reference plane P, in non-filled state of the pouch 2. In the illustrated embodiments, the plates 12A, 12B form a covering portion 8 able to be resiliently displaced, away from the protecting body reference plane P as far as a middle region MR is concerned, by a pushing effect of the walls W1, W2 of the pouch 2 during a step of filling the flexible pouch 2. The covering portion 8 thus may have swollen conformations, which are not stable conformations of the protecting body 12, 112, 212 when the pouch 2 is in non-filled state. The plastic material of the protecting body 12, which is typically a non-porous plastic material, is configured to resiliently return to a stable planar configuration, in which the interspace between the plates 12A, 12B is planar, i.e. without any increase in spacing between the plates 12A, 12B. Each plate 12A, 12B is here a single molded piece of non-porous plastic material.

Figure 7A:
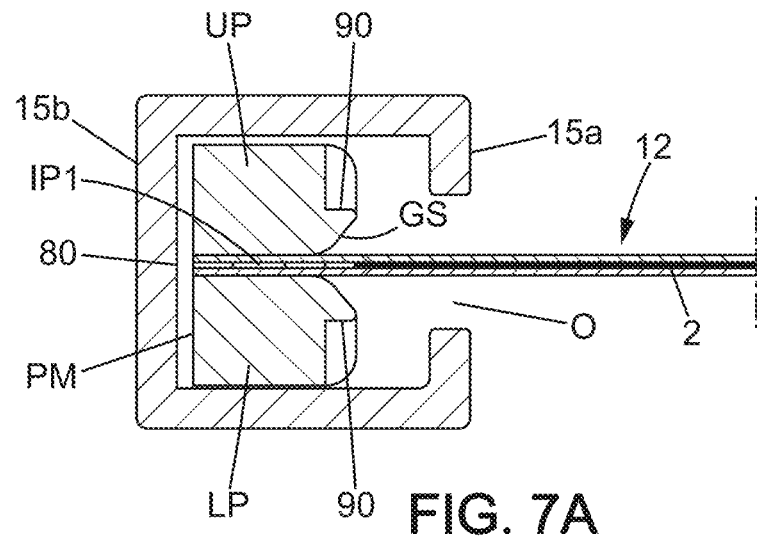
FIG. 7A is vertical cut view showing a positioning member suitable to form a stopper, configured to slide inwardly in a profile cavity with a limited stroke while retaining a portion of the peripheral margin of the protecting body.
Figure 7B:
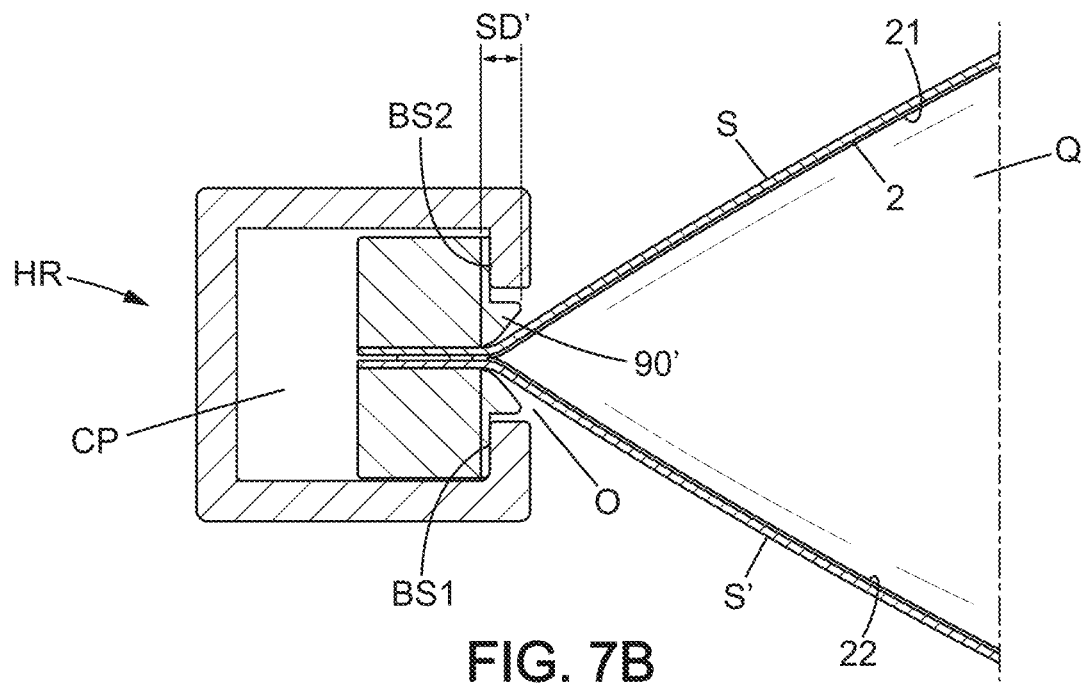
FIG. 7B is same vertical cut view as in FIG. 7A, showing an abutment position so that the positioning member stops inward movement of the corresponding peripheral margin portion of the protecting body.

The system 1 is suitable for containing, freezing/thawing a biopharmaceutical composition Q (see FIG. 7B). Referring to FIGS. 4A and 6A, such system 1 is here horizontal, using a horizontal frame. However, this system may also be vertical in variants, so that the pouch 2 can be stored vertically in a cavity of a vertical frame-like holder (see for instance pouches described in WO 03037082, received vertically by use of rigid slotted frames). Use of a rectangular frame 15, provided with slots or cavities CP opening inwardly, may be of interest, in order to form a compact holder, able to accommodate respective margin portions of a storage unit 10.

Figure 1:
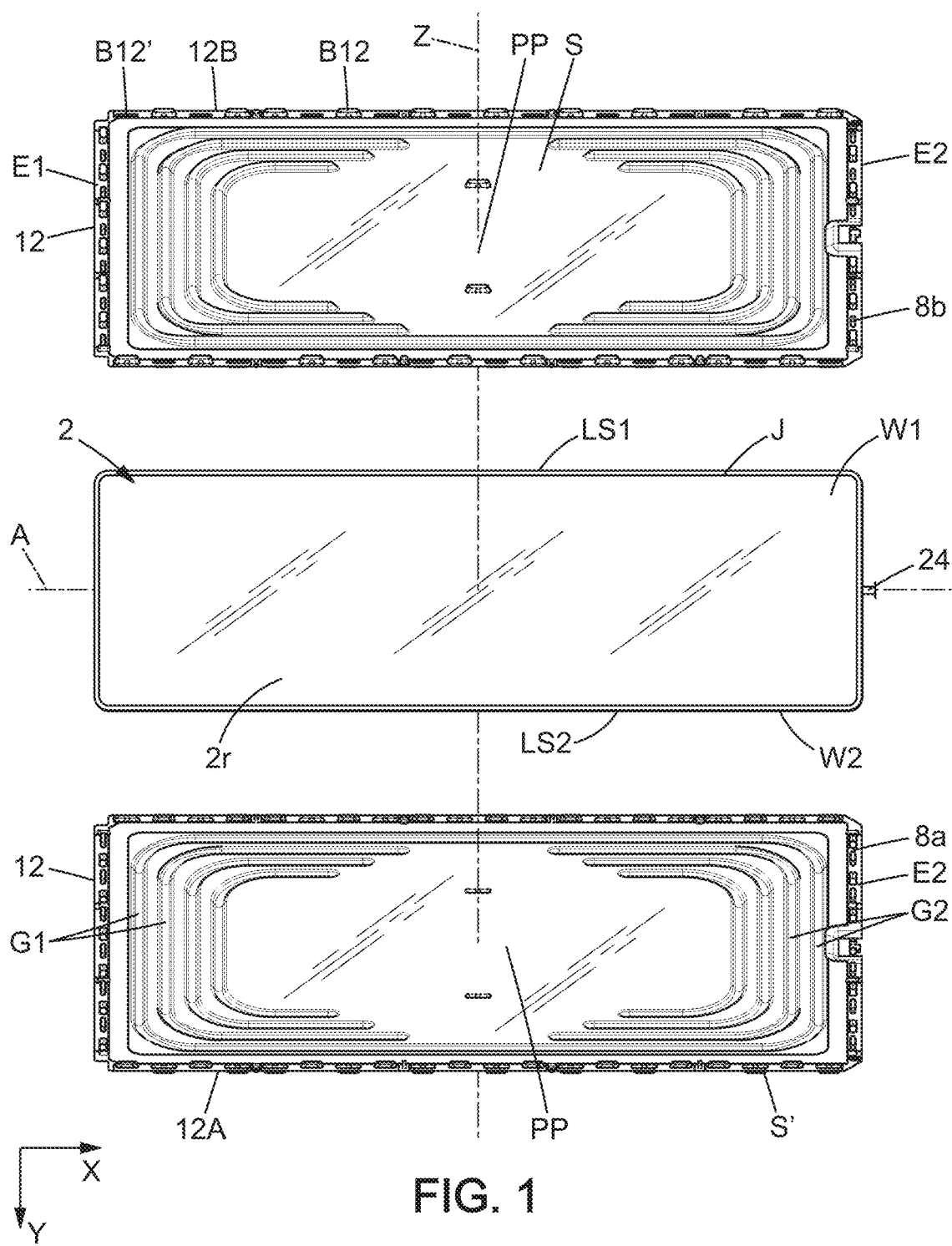
FIG. 1 is a perspective view of a storage unit in accordance with a first embodiment of the invention, before assembling the two plates of the protecting body.

The flexible pouch 2 is typically a 2D-type pouch, delimited by two longitudinal sides LS1, LS2 and having a substantially rectangular shape without predefined folds on its two main outer faces, as illustrated in FIG. 1 (empty pouch). Accordingly, the pouch 2 extends substantially planar in non-filled state. The pouch 2 may have two main walls W1, W2. These walls W1, W2 may be directly welded one to each other at a weld or peripheral seal J to delimit an interior volume for containing the biopharmaceutical fluid Q. More generally, the flexible pouch 2 may be of any suitable material for containing a biopharmaceutical composition Q and forms a freezer bag, which may be of large capacity, typically superior or equal to 5 L. More generally, the flexible pouch 2 is of a first capacity and the pouch 2 can expand to have an increase in thickness at least in a middle region away from the four pouch corners, such thickness increasing with the level of filling the pouch 2.

Referring to FIG. 1, the flexible pouch 2 extends in a main plane XY which is, here, the horizontal plane. The pouch 2 has a longitudinal axis A parallel to its long sides, which are here the two longitudinal sides LS1, LS2 in the non-limiting illustrated embodiment. The flexible pouch 2 is sandwiched by the plates 12A, 12B and cannot be removed without detaching at least one of the two plates 12A, 12B, here by disconnecting the plate margin portion of annular shape from the plate margin portion of same annular shape (the plates are secured to each other, without specific fixation between the pouch 2 and any one of the plates). A holding and retaining assembly HR may be provided, additionally to the attachment system 18, for holding the unit composed of the protecting body 12 and the attachment system 18. The assembly HR is here provided with the frame 15 that includes slides, frame profiles 93, 94 or similar slotted structures for holding the storage unit 10 at its peripheral margin 80. FIGS. 4A-4B show an exemplary frame 15 of such assembly HR.

Typically, the receiving part 2r of the containing pouch 2 for receiving the biopharmaceutical composition Q cannot be in contact with the rigid structures of the holding and retaining assembly HR, thanks to the protecting body 12, 112 or 212. In the assembled state, the protecting body 12, 112, 212 entirely covers the receiving part 2r of the pouch 2.

Figure 6E:
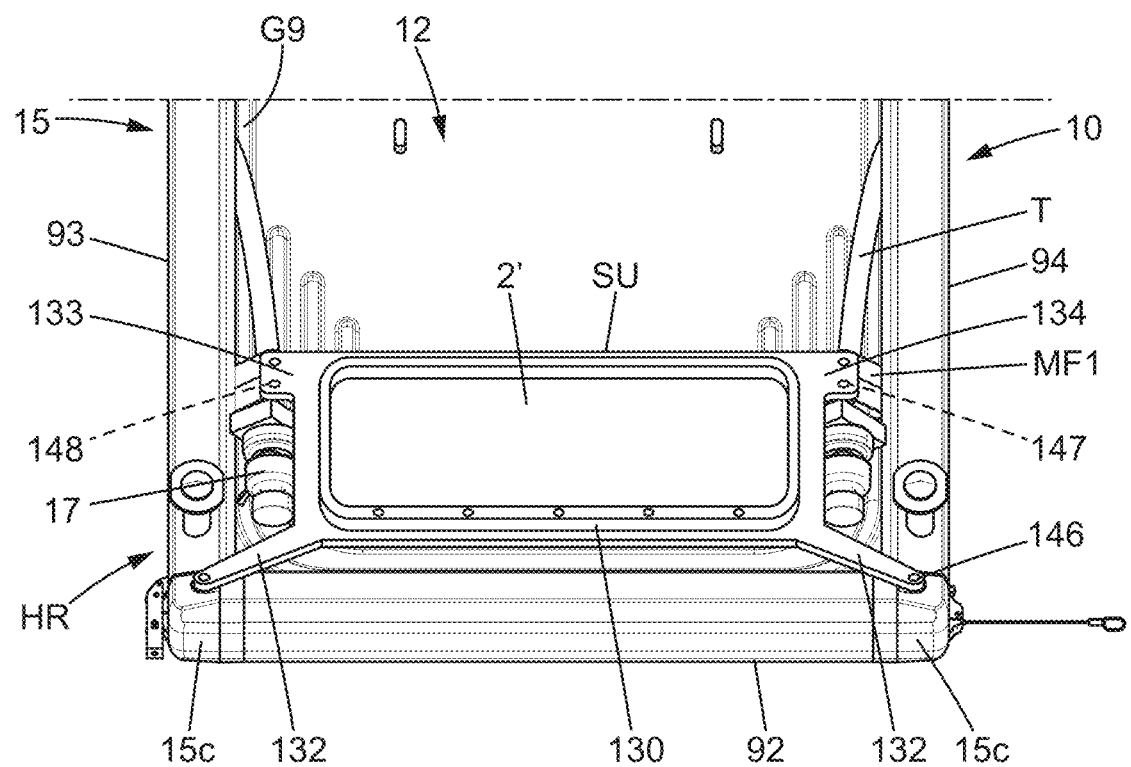
FIG. 6E illustrates a top view of a part of the freeze/thaw containment system of FIG. 6A, with a sample unit attached to the system.

The storage unit 10 provides efficient protection in freezing, storing and thawing operations, while the biopharmaceutical composition Q is contained in the receiving part 2r of the flexible pouch 2. The covering portion 8 of the protecting body 12 is not as flexible as the receiving part 2r of the flexible pouch 2, due to a difference in material (more rigid for the two pieces forming the plates 12A, 12B). When placed horizontally and maintained by the holding and retaining assembly HR, the two plates 12A, 12B respectively form a lower surface and an upper surface of the protecting body 12, 112, 212. At least one amongst the lower surface and the upper surface is a storage unit outer surface, which may be optionally provided with fastening members for allowing fastening of a bag 2', directly or indirectly. In illustrated embodiments, such fastening members 146, 147, 148 for securing a bag 2' are selectively provided on the frame 15, for instance on corner parts 15c that belong to the frame 15. The corner parts 15c may be under the form of:

pieces interposed between two perpendicular profiles 92, 93, 94 of the frame 15 (as shown in FIGS. 6A and 6E in particular), end parts of such profiles, or additional pieces mounted on some of the profiles.

Referring to FIGS. 6A and 6E, the storage unit 10 can also support a bag 2', thanks to the holding and retaining assembly HR, or independently from the holding and retaining assembly HR, or by combining fastening members of the protecting body 12 and fastening members of the assembly HR in some variants. This bag 2' may contain a composition representative of the biopharmaceutical composition Q. The capacity of the bag 2' is a second capacity lower than the first capacity, preferably of a lower order of magnitude (i.e. at least 10 times lower). The bag 2' may be provided with a casing 130, which may be relatively rigid. Such casing 130 may cover a pouch forming a containing part 200 of the bag 2'.

The bag 2' may be provided with fastening elements 132, 133, 134 cooperating with the fastening members 146, 147, 148, in order to have the bag 2' fastened (directly or indirectly) to the protecting body 12, 112, 212 and/or to the frame 15. In order to have the casing 130 affixed to extend along one of the outer surfaces S, S' of the storage unit 10, the fastening elements 132, 133, 134 can be distributed around a containing part 200 of the bag 2', here around the casing 130 that may include a compartment for housing the containing part 200. The containing part 200 of the bag 2' is the part of the bag 2' which defines the second capacity.

As illustrated in FIGS. 1-4B, the flexible pouch 2 may be directly protected (sandwiched with direct contact) by two plates 12A, 12B of a protecting body 12. The positioning members PM are provided at the peripheral margin 80, in order to not interfere with change in conformation of the covering portion 8 of the protecting body 12, 112, 212.

Each pouch 2 may be filled with a solution, fluid composition Q, to be frozen and held with slight compression between the two plates 12A, 12B that serve as heat-exchange surfaces. For this purpose, the plates 12A, 12B completely cover the pouch 2, at least in the fluid receiving part 2r, i.e. region defining the interior volume of the pouch 2 (i.e. typically all the walls W1, W2 with possible exception of the annular seal J and optional outer extension(s)), as shown in FIG. 1 in particular. In the illustrated embodiments, the pouch 2 is entirely covered by a protecting body 12, 112, 212 which is formed by the two plates 12A, 12B. During freeze/thaw operations, the plates 12A, 12B are cooled/heated by circulating heat transfer fluid, for instance from an external, programmable refrigeration unit. The slight compression (containment effect) provides improved contact and heat transfer, resulting in a frozen pouch having the general shape of a pillow (see FIGS. 4A and 6A in particular).

The pouch 2, sandwiched between the plates 12A, 12B may be placed in a frame 15, here a rigid frame compatible with temperatures below 0° C. (preferably not becoming brittle). The frame 15 is of interest so as not to damage the material inside during handling and transport. Referring to FIGS. 4A and 6A, the frame 15 may be part of a supporting structure. Here, the frame 15 is a modular part of a device or shelf (see FIG. 10) that may be located in a freezing apparatus. Rollers (not shown) may be provided for facilitating transportation, in some options. The frame 15 is typically a rectangular protective frame, leaving the outer surfaces S, S' of the protecting body 12 exposed but forming four protecting sides of the storage unit 10. The frame 15 may be included in a holding and retaining assembly HR, which also includes or accommodates positioning members PM fastened to the peripheral margin 80 of the protecting body 12, 112 or 212, as illustrated in FIGS. 4C-4D, 4F and 8 in particular. The assembly may comprise a plurality of feet 115, possibly of tubular shape and suitable for stacking. FIGS. 4A and 11c illustrate non-limiting examples of integration of feet 115, suitable for obtaining a shelf structure such as shown in FIG. 10.

In some options, the spacing between two successive frames 15, at least between the frame long sides, creates an inter-unit open space to improve airflow for freezing/thawing the content of the pouches 2. Such vertical interspace, as illustrated in FIG. 10, also provides accessibility to the protecting body and its edges for wipe down.

It also provides accessibility to a bag 2' or similar sample unit SU that can be fixed on an outer surface of the protecting body 2, 112, 212, as illustrated in the non-limiting example of FIG. 6A and FIG. 6E.

More generally, the pouch 2, the protecting body 12, the bag 2' or similar sample unit SU if fastened to the protecting body, and the frame 15 may define a freeze/thaw containment system 1, in which outer surfaces S, S' (here corresponding to the lower surface S' of the lower plate 12A and the upper surface S of the upper plate 12B) remain exposed (uncovered), while the flexible pouch 2 is placed inside the storage unit 10, covered by the two plates 12A, 12B. The protecting body 12 has a peripheral margin 80 which is engaged in interspaces of the holding and retaining assembly HR. The storage unit 10 is suitable for use in freezing, storing and thawing biopharmaceutical fluid/composition Q contained in a flexible pouch 2, the fluid being typically introduced after assembling the storage unit 10 with the flexible pouch 2, which is typically a disposable pouch, housed in the protecting body 12.

In FIGS. 4B, 6A and 7B, it can be seen that the pouch 2 is inside the protecting body that is retained by frame profiles 91, 92, 93, 94. Use of four rigid profiles is of interest for forming a rectangular frame 15. Optionally, the pouch 2 may be of the Flexboy® type, and thus is a sterile, single-use, disposable container, adapted to be enclosed by the frame 15 obtained after assembling the profiles 91, 92, 93, 94 or similar holding elements.

In some options the holding and retaining assembly HR may have less than four members, so as not to form a rectangular frame. For instance, only three members may be sufficient, with a transverse member interconnecting two longitudinal covering parts 31, 32 parallel to the longitudinal axis A of the pouch 2. FIG. 3 only shows two covering parts 31, 32 that may be integral with feet or which may be associated to a transverse structure member. In some options, the covering parts 31, 32 may extend vertically. In the illustrated embodiments, the covering parts 31, 32 extend horizontally, which may be preferred when the pouch contains more than 50 L, for instance about 75 L or at least 100 L.

Referring to FIGS. 3, 4B, 5A-5B and 7A-7B, the pouch 2 may have a form or shape that is initially planar in empty state. The pouch 2 is flexible, in order to be inflatable, and may be made from a pair of flexible sheets (which form the respective walls W1, W2), having a rectangular or other plan form, and joined together at the four peripheral edges, to provide a containment volume (interior volume for composition Q) between the sheets 21, 22, which are spaced by a spacing in a filled state. One or more openings or ports 24 may be provided, for example formed as closable tubes between facing parts of said peripheral edges of the sheet, to allow the pouch 2 to be filled or emptied.

The pouch 2 is also designed to provide a high surface area/volume ratio at a thin thickness or spacing. By way of non-limiting example, a pouch 2 may have rectangular dimensions of about 600 mm by about 1300 or 1400 mm, and/or a holding volume of between about 10 liters and about 120 or 200 liters (preferably between 50 and 120 liters), and/or a spacing or pouch thickness (height along Z direction) of between about 8 or 10 mm to about 25 or 30 mm.

Each pouch 2 may be made from any suitable biologically compatible material, and which preferably facilitates heat transfer between the inside and the outside of the pouch 2. To reduce or avoid damage to the pouch 2 during cryopreservation due to the expansion of the biopharmaceutical material, it is preferred that the material would have a glass transition temperature that is below that of the biopharmaceutical material. By way of non-limiting example, each pouch 2 may be made from a multilayer composite material only made of thermoplastic material, for instance including polyethylene (at least a layer of PE).

The protecting body 12 and the flexible pouch 2 comprise a longitudinal direction X and a transversal direction Y. The protecting body 12 and the flexible pouch 2 comprise each longitudinal and transversal sides. The longitudinal axis X1 of the protecting body 12 may be placed in a median vertical plane separating two symmetrical halves for each plate 12A, 12B of the protecting body.

The pouch 2 optionally includes one or more tubes T joined to a front end (at a transversal side) that extends transversally relative to the longitudinal sides LS1, LS2. More generally, the pouch 2 may comprise one hose/tube or any suitable number of tubes that are connected to a periphery of the useful part of the pouch 2. This useful part is here formed by the two main walls W1, W2.

Protecting Body

Referring to FIGS. 1 and 3-4A, the protecting body 12 or 112 comprises or consists in two plates 12A, 12B for protecting the flexible pouch 2. The plates 12A, 12B are entirely separate, here without hinging or connecting part. Typically, the plates 12A, 12B are two separable pieces. These pieces are relatively rigid, for instance sufficiently rigid so that they cannot form folding lines with bending angle of more than 45°. The plates 12A, 12B are thus configured to remain relatively flat. The protecting body 12, 112, 212 comprises a longitudinal axis X1 and has four sides 120a, 120b, 120c, 120d, the four sides comprising two longitudinal sides 120c, 120d extending parallel to the longitudinal axis X1 and two other sides that include a first end side 120a, and a second end side 120b each perpendicular to the longitudinal axis X1.

Referring to embodiments of FIGS. 1-3, in each plate 12A, 12B, a first group of ribs is provided with ribs R1, R2, R2', 800 arranged close to the peripheral margin 80. An optional second group of ribs may be provided with ribs R3, R4, 83, 84, 85, 86 arranged at a greater distance from the peripheral margin 80. Such ribs of the second group may surround one or two panel portions PP, PP1, PP2, which are typically forming rectangular panels, in each outer surface S, S' of the protecting body 12, 112.

In some variants, the number of ribs may be reduced or the ribs may be removed.

In the illustrated embodiments, the protecting body 12, 112, 212 preferably has an attachment device/system 18 for fastening the two plates 12A, 12B so that in an assembled state of the two plates, the protecting body 12, 112 comprises a peripheral margin 80 that extends annularly in a protecting body reference plane P as illustrated in FIGS. 2A, 3 and 4A-4B. In some options, the peripheral margin 80 that extends in an interior interspace delimited by the frame 15 is typically a margin without ribs. In variants, one or more ribs R1 adjacent to the margin part for mutual attachment of the plates 12A, 12B may extend in such interspace. Unlike the welding seals of the flexible pouch 2, forming an annular margin that is flat, without any rib or relief, the peripheral margin 80 may comprise reliefs that form all or part of the attachment system 18. As illustrated, the reliefs are narrow as compared to the elongated ribs R1, R2, R2', R3, R4, 83, 84, 85 provided in the covering portion 8 of the protecting body 12, 112.

The protecting body may be provided with:
a first end side 120a, which is composed of the ends E1 of the two plates 12A, 12B in the assembled state of the protecting body 12, 112, 212, and
a second end side 120b, which is composed of the ends E2 of the two plates in the assembled state of the protecting body 12, 112.

The one or more ports 24 may protrude axially outward from the second end side 120b. Here a part of the pouch front edge is thus accessible.

In empty state of the pouch 2, the two plates 12A, 12B respectively form a first surface S' and a second surface S of the protecting body 12, 112 covering the pouch 2. When having a substantially horizontal configuration, the first surface is a lower surface and the second surface is an upper surface. In some option (not illustrated), all or part of the fastening members 146, 147, 148 can be provided on one of these surfaces S, S' near an end side chosen amongst the first end side 120a and the second end side 120b.

At least one amongst the lower surface S' and the upper surface S may be a surface having a plurality of ribs distributed in two opposite parts of the surface, which are longitudinally opposite parts. Preferably, the ribs of this plurality include first transverse rib portions 4 proximal to the first end side 120a and second transverse rib portions 6 proximal to the second end side 120b.

Such transverse ribs provide an accordion effect due to width of the corresponding grooves G1, G2 formed by the ribs and/or height of the ribs (depth of the grooves G1, G2). This facilitates local expansion of the plates 12A, 12B despite the planar structure of the peripheral margin 80 forming the protecting reference plane P. Typically, in corner regions CR, the first and second transverse rib portions 4, 6 have a height decreasing with decreasing space from the corner vertices of the plate having such rib portions 4, 6. Accordingly, too great expansion that could create undesirable folds (along diagonal lines) may be limited or prevented when having height reduction for the corner rib portions, extending in the corner regions CR. In other words, accordion effect may be practically reduced in the four corner regions CR in each plate 12A, 12B. More generally, structuring of the plates 12A, 12B, using first and second transverse rib portions 4, 6 is helpful, in order to facilitate spreading of fluid toward the margin 80 and toward the corners of the protecting body 12, 112 when filling the flexible pouch 2 sandwiched between the plates 12A and 12B.

This is of interest, in order to have or improve a belly retention effect. Indeed, the more the fluid can be distributed toward the four corners, the less bulged is the pouch 2 in a middle region. The protecting body 12, 112 is typically able to move in interspaces of the holding and retaining assembly HR, as described in more detail below. Besides, the structuring effect of the ribs may prevent folding lines to form substantially along the diagonals DL1, DL2, when difference in thickness/expansion between the middle region including the center C of the protecting body and the covering portion edges is too pronounced.

Some detailed embodiments of a protecting body 12 or 112 provided with a ribbing pattern will be described hereinafter.

The plates 12A, 12B as illustrated in FIGS. 1, 2A-2B, 4A-4C, 4F-4G and 8 correspond to a first embodiment of the protecting body 12, in which several ribs are provided. In each outer surface of the plate, the ribs are provided so that the inner face is provided with grooves. Some grooves G1, G2, such as shown in FIG. 1, are including transverse groove portions extending perpendicular to the longitudinal axis X1 and close to the opposite end sides 120*a*, 120*b* of the protecting body. An annular rib R1, protruding upwardly in the outer surface S or S', may be provided to define the groove G1 which is of annular shape on the plate interior surface. Two separate ribs R2, R2' protruding upwardly in the outer surface S or S', may be provide to define the one or two grooves G2 which are each of annular shape or partly annular shape on the plate interior surface.

Thanks to the ribs R1 and R2, R2', a pair of transverse rib portions 4, 6, here parallel to Y-axis direction (perpendicular to the longitudinal axis X1) may be arranged close to the respective end sides 120*a*, 120*b*. In other words, these ribs form the first transverse rib portions 4 proximal to the first end side 120*a* and the second transverse rib portions 6 proximal to the second end side 120*b*.

Referring to FIGS. 1-2A, it can be seen that each plate 12A, 12B may be rectangular with four corner regions CR, two virtual diagonal lines DL1, DL2 (diagonal lines of the plate) intersecting each a pair of corner vertices of the four plate corners. More precisely, each of the two virtual diagonal lines DL1, DL2 intersect:
 a first series of corner ribs C1, C2 proximal to the first end side 120*a* and protruding outwardly along a direction perpendicular to the protecting body reference plane P, and
 a second series of corner ribs C1, C2' proximal to the second end side 120*b* and protruding outwardly along a direction perpendicular to the protecting body reference plane P.

Each of the corner ribs C1, C2, C1', C2' is curved and connects two rib portions that are perpendicular one to each other. Here the annular rib R1 thus may include two pair of corner ribs C1, respectively C1'.

While embodiments of FIGS. 1, 2A-2B, 4A show ribbing patterns, in which the ribs may be considered as peripheral ribs, arranged around a central panel portion PP of the plates 12A, 12B, FIGS. 3 and 6A show that ribs may be provided in a middle region MR, possibly extending transversally to separate two panels PP1, PP2 of a same plate.

While same ribbing pattern is provided in the two complementary plates 12A, 12B in embodiments of FIGS. 1-3 and 4A-4B, 6A, some differences may be provided in variants. Optionally, one or two of the plates may be deprived of ribs.

The plates 12A, 12B form each a stiffening layer when overlapping, and preferably entirely covering, the main walls W1, W2. The thickness of each plate 12A, 12B before thermoforming is of about 1.27 mm and/or may be lower than 2 mm, with provision that the plastic material of the plates has a density superior to 1.10 g/cm$^3$, preferably superior to 1.15 g/cm$^3$ (typically without being above 1.5 or 1.6 g/cm$^3$). Plate material may have a tensile strength at break, which is typically between 45 and 75 MPa, for example in the range 50-60 MPa, typically 52-59 MPA (standard test ASTM D638). Plate material may have a tensile strength at break between 45 and 60 MPA and a Young's Modulus comprised between 1250 and 1550 MPa, both along transverse direction (TD) and machine direction (MD).

While the illustrated embodiments show a protecting body 12 covering entirely the two main walls W1, W2 by the covering portion 8, other size may be used for the covering portion 8. For instance, the protecting body 12 could only cover a transverse band portion of each wall W1, W2, at a distance from one of the two pouch opposite edges. Besides, one or more complementary protecting bodies could be used to cover at least one of the end parts of the walls W1, W2.

Details of Embodiments for the Attachment System for Attaching the Plates Together The protecting body 12 may have a covering portion 8 for covering the pouch 2 and two opposite margin portions 8*a*, 8*b* at two longitudinal sides 120*c*, 120*d* of the protecting body 12. In non-filled state of the pouch 2, the protecting body 12 extends flat and remains flat along a protecting body plane P. The plates 12A, 12B remain attached at several location of the peripheral margin 80 during handling of the system 1, thanks to an attachment system 18.

The protecting body 12 may be transparent, the pouch 2 being also transparent for instance. The plates 12A, 12B can have a general curvature but cannot easily fold (flexibility being substantially as low as PET). The peripheral margin 80 may form an annular attachment area, in which no folding is permitted.

Referring to FIG. 2, the protecting body 12 is also provided with an attachment system 18 for fixing the two plates 12A, 12B to each other, around the covering portion 8. The plates 12A, 12B may be removably fixed to each other by the attachment system 18 distributed in the peripheral margin 80.

Optionally, the attachment system 18 may comprise a plurality of snap buttons. The plates 12A, 12B are provided with several interlocking means, for instance arranged in pairs with one of the two plates 12A, 12B comprising a first element of one snap button and the other plate comprising a second complementary element of one snap button. Referring to FIG. 2A, the second element 18*b* (possibly a male element) engages the first element 18*a* (possibly a female element) in a direction parallel to the vertical axis Z. More generally, it is understood that any interlocking means formed as reliefs in the peripheral margin 80 may be distributed in the plates 12A, 12B. Each of the reliefs of a given plate 12A protruding toward the other plate 12B can be fitted, possibly loosely fitted, in a corresponding hollow relief protruding away from the plate 12A; and vice versa.

Alternatively, the attachment system 18 is a non-removable system, which means that, once the two plates 12A, 12B are fixed to each other, it is not possible anymore to detach the two plates 12A, 12B one from each other.

Having reliefs in the attachment system 18 only included in the peripheral margin 80 may be advantageous for a protecting body covering a pouch of large size, thus minimizing the pieces and facilitating fastening operation. Moreover, reliefs formed by such integral attachment system 18 may serve as discrete anchoring parts for easily placing and fixing the positioning members PM, as it will described farther when referring to FIGS. 2B and 4B-4G.

In the non-limiting embodiment of FIGS. 1-2A, the protecting body 12 may comprise:
 snap buttons 18*a*, 18*b* on transversal sides 120*a*, 120*b* and on the two margin portions 8*a*, 8*b*;
 and/or apertures 102 (see FIGS. 5A-5B and 7A) for receiving an insert piece IP or similar anchoring member that is not included in the plates 12A, 12B.

In options using snap buttons or similar fastening parts included in the plates 12A, 12B, such fastening parts can be symmetrically arranged on the transversal ends of the two plates 12A, 12B. Alternatively, the protecting body 12 may comprise more snap buttons on the front side 120*a* that in the rear side 120*b*.

More generally, the attachment system 18 may typically comprise any suitable mechanical fasteners arranged between the covering portion 8 and the longitudinal sides 121, 122. Typically, the two opposite margin portions 8*a*, 8*b* may be considered as part of a fastening assembly provided to prevent any shifting in position between the two plates 12A, 12B once they are mutually fastened at least in the two margin portions 8a, 8b.

Referring to FIGS. 1, 2A-2B and 4B-4C, the attachment system 18 has first and second elements 18a, 18b, which may be made identical or similar, and respectively distributed in the lower plate 12A and in the upper plate 12B. With such configuration, the plates 12A, 12B may be identical. The first elements 18a belong here to a first plate 12A, while the second elements 18b belong to a second plate 12B. The interlocking means may be formed, in the peripheral margin 80, with an alternance of boss portions B12 protruding outwardly and boss portions B12' protruding inwardly.

Such boss portions B12, B12' may be hollow, so that it can simultaneously act a male and female members. For at least a part of these boss portions, each boss portion may be simultaneously involved as:
  male member for guiding and fixing parts LP, UP of the positioning members PM, PM',
  and female member for the interlocking function in the attachment system 18.
And/or, for at least a part of the boss portions, each boss portion may be involved, each as:
  male member that is fitted/received in the hollow of a corresponding boss portion (of the other plate),
  and female member for guiding and fixing parts LP, UP of the positioning members PM, PM'.

It can be seen that the boss portions B12' are thinner than the boss portions 12. They may be removably fitted inside the boss portions B12'. In a given plate 12A or 12B, the boss portions B12' are orientated inwardly to protrude at the opposite from the plate outer surface. The boss portions B12' can be snap-fitted inside the hollow of the boss portions B12, so that they can protruding beyond the reference plane without protruding beyond the other plate (no need for a through-hole in the plates 12A, 12B). More generally, the first and second elements 18a, 18b may be configured so that the protecting body 12 is a two-piece body, able to extend along its reference plane P without accidental detachment to protect the pouch 2, without any additional fastening means. The positioning member PM, PM' can be considered as intermediate pieces for interconnecting the protecting body 12 to the frame 15.

The plugging of the positioning members PM, PM' on the peripheral margin 80 is sufficient to have the parts LP, LP', UP, UP' secured to the corresponding plate 12A or 12, with a clamping effect due to the boss portions 12, typically using clamping outer reliefs RS formed on side wall of the boss portion B12, as illustrated in non-liming example of FIG. 2B. In other words, the lower parts LP, LP' may optionally be secured to the lower plate 12A and the upper parts UP, UP' may optionally be secured to the upper plate 12B, before fastening the plates 12A, 12B together.

Here, the boss portions B12' may be subsequently inserted in the hollows of the boss portions B12 to form the protecting body reference plane P. The inner wall delimiting the hollow of a boss portion may slightly taper toward the access opening, so as to provide a retaining effect without preventing sufficient insertion of the boss portion B12'. The outer clamping reliefs RS may be axially and radially engaged onto the tapering part of the inner wall.

While the drawings show attachment of the pieces forming the positioning members PM, PM' by a substantially linear plugging action using two plugging areas, other coupling can be involved, for instance by rotating such pieces around an axis that is parallel to Z-direction, possibly after firstly engaging a pivot socket or pivot insert of such piece around a coupling relief formed in the peripheral margin 80. The final position of the pivoting positioning member may be locked, using a clip and/or an abutment part.

Here, boss portions B12, B12' are provided for having the plates 12A, 12B fixed one to each other in removable manner, the boss portions B12' acting as male members in the interlocking of the attachment system 18 for cooperating with the corresponding hollows of the boss portions B12. Typically, the first boss portions B12 are delimiting hollows so that the second boss portions B12' are received with plastic retaining contact. Here, the second boss portions B12' are projections (preferably hollow projections) protruding inwardly from the corresponding plate 12A or 12B, perpendicular to the plane P.

More generally, the plates 12A, 12B may be removably fixed to each other by any suitable attachment system 18. Such system 18 may also be of the type that can be specifically seen (schematically illustrated) in FIGS. 3, 5A-5B and 6C. In some options, the plates 12A, 12B support interface pieces that are overlapping the attachment region defined by the attachment system 18, without interfering with the attachment between the two plates 12A, 12B. Such interfaces pieces, possibly including a resiliently deformable part or a discontinuous face for contact with the abutment surfaces, are removably mounted on the peripheral margin 80. In other options, all or part of these interface pieces, interfacing the peripheral margin 80 and the covering parts of the holding and retaining assembly HR, act as fasteners for maintaining the plates 12A, 12B in a planar state around the covering portion 8.

As can be seen on FIGS. 2A-4G, 6A-6B and 7A-7B, when the two plates 12A, 12B are fixed to each other, they sandwich the flexible pouch 2. The planar plate 12A, which forms the lower surface S' of the protecting body 12, presses the lower surface of the flexible pouch 2, with respect to the vertical axis Z. Similarly, the planar plate 12B, which forms the upper surface S of the protecting body 12, presses the upper surface of the flexible pouch 2, with respect to the vertical axis Z. The two plates 12A, 12B may have planar dimensions which are substantially identical to the ones of the flexible pouch 2.

Holding and Retaining Assembly

Referring to FIGS. 3, 4A-4B, 4F and 6A-6E, the holding and retaining assembly HR comprises a frame 15 and positioning members PM, PM' that either cooperate with or are part of the attachment system 18. The positioning members PM, PM', here covering the attachment system 18 by sandwiching parts of the peripheral margin 80, are able to move relative to the frame 15 acting as a stationary part of the holding and retaining assembly HR. In some embodiments, the two longitudinal covering parts 31, 32 comprise profiles and may be considered as belonging to the holding and retaining assembly HR. The positioning members PM, PM' may be introduced in profiles of the frame 15 or may be attached to similar covering parts 31, 32 before assembling the assembly HR (typically before assembling a frame 15).

In options of FIGS. 5A-5B, 7A-7B and 8, the positioning members PM may include an insert portion or be associated to an insert piece IP, so that they belong to the attachment system 18 for maintaining the protecting body 12 in an assembled state. In such options, the plates 12A, 12B are provided with through-holes. In some variants, the plates 12A, 12B may include over-molded parts integral with the peripheral margin 80, in order to form the positioning members that have a retaining effect when housed in or engaged in any suitable manner with the covering parts 31, 32 of the assembly HR.

More generally, the two covering parts, such as shown in FIG. 3, are arranged to maintain two longitudinal margin portions 8a, 8b of the peripheral margin 80, while allowing the two plates 12A, 12B moving, extending, and shrinking in a transverse direction belonging to the protecting body reference plane P. As illustrated in FIG. 4A, 6D-6E, the two longitudinal covering parts 31, 32 may comprise two profiles 93, 94 each delimiting an interior cavity CP. In non-limiting embodiments, the interspaces may be respective interior cavities CP of such covering parts. Each of the two longitudinal covering parts 31, 32 may include a profile that is substantially C-shaped or U-shaped to delimit one of the interior cavities CP.

Referring to FIGS. 2A-2B and 6A, it is understood that the pouch 2 is sandwiched between the plates 12A, 12B but without interfering with the hose(s) or tube T each provided with an end connector 17. The protecting body 12, 112, 212 may be firstly assembled and, then the two protective parts 31, 32 are assembled to complete or cover the attachment device 18.

Typically, the holding and retaining assembly HR comprises a frame 15, here of rectangular shape, provided with four sides. The longitudinal covering parts 31, 32 may be protected in profiles 93, 94 forming the two longitudinal sides of the frame 15. Other covering parts provided along transverse sides of the protecting body 12, 112, 212 may also be included in the attachment system 18. Optionally, such other covering parts may be housed/protected in profiles 91, 92 forming the two transverse sides of the frame 15.

More generally, several profiles may form all or part of the frame sides. Preferably, at least four rigid profiles 91, 92, 93, 94 arranged in rectangular manner form the four sides. Two of the four profiles are included in or form the two longitudinal covering parts 31, 32. These two profiles 93, 94 are formed as two longitudinal slides for receiving each at least three of the positioning members PM, which are separate and distributed along a length of the frame 15. Optionally, the two other profiles 91, 92 may also form slides, here transverse slides, to accommodate the transversal sides 120a, 120b of the protecting body 12, 112, 212. Similar positioning members PM, PM' may be slidably mounted in the rail-like profiles 91, 92.

The holding a retaining assembly HR can maintain the protecting body horizontally or vertically, the frame 15 being also of interest for forming a peripheral protection around the protecting body 12, 112, 212. The peripheral frame 15 houses the internal positioning members PM, PM' that have size along Z direction that is greater than the corresponding size (along same direction) of the opening at the open side of the profiles 91, 92, 93, 94. While four similarly constructed profiles 91, 92, 93, 94 are here provided to house positioning members PM on each of the four sides, variants with one or two sides without such positioning members PM may be provided. Besides, variants with another kind of covering parts 31, 32 mays be provided, either with ability to have a shrink management of some sides of the protecting body 12, 112, 212, or without possibility to have such shrink management (for example if the capacity of the pouch 2 is relatively low).

The structure shown in FIG. 4A is of interest for relatively large capacity pouches 2, which could have a significant bulge B without any shrink-management at the peripheral margin 80.

Now referring to FIGS. 4A-4G, 5A-5B, 6A-6D and 7A-7B, it will be described exemplary embodiments for forming the positioning members PM as stoppers preventing too great inward displacement of some regions of the peripheral margin 80, when the pouch 2 is more and more filled. Here, the frame 15 is provided with abutment surfaces AB1, AB2 included in abutment members or rims BS1, BS2. Each abutment members may delimit an inner access to a housing, in which the positioning members PM, PM' extend. Here each profile 91, 92, 93, 94, forming a side of the frame 15 may be provided with an open end suitable for introduction of a respective side of the protecting body 12, 112, 212 inside the housing (side chosen amongst the four sides). Such open ends may be each closed by a corner section 15c fastened to a profile end support. The inner open sides, formed by inner opened sections 15a of the frame 15, are not used for assembling or disassembling steps, due to presence of the abutment members BS1, BS2 that prevent any possibility for the positioning members PM to be inserted inside or extracted outside the profiles through the inner open sides. Indeed, at an inner face of each profile 91, 92, 93, 94, there is at least one abutment member BS1, BS2 extending transversely relative to the protecting body reference plane P.

Here in the illustrated embodiments, the positioning members PM mounted in the long margin portions 8a, 8b of the peripheral margin 80 have a size, at least along X and Z direction, which is constant. In some variants, the inner open sides can have at least one passage opening allowing insertion of positioning members PM having a first compact configuration in which they are secured to the peripheral margin 80. After such insertion, the positioning members are expanded to have a second configuration preventing extraction of the positioning members through the inner open sides. In such second configuration, the positioning members remain secured to the peripheral margin 80 by a fastening part, which is typically a stationary part. A telescopic configuration of the positioning members (with telescopic expansion available along X or Z axis direction), an expandable material or a hinged structure may be used, to have such expansion effect. In their second configuration, the positioning members PM can be retained by the abutment members BS1, BS2. The frame 15 may have another opened section for accessing and actuating, preferably reversibly, the expansion effect.

Figure 4C:
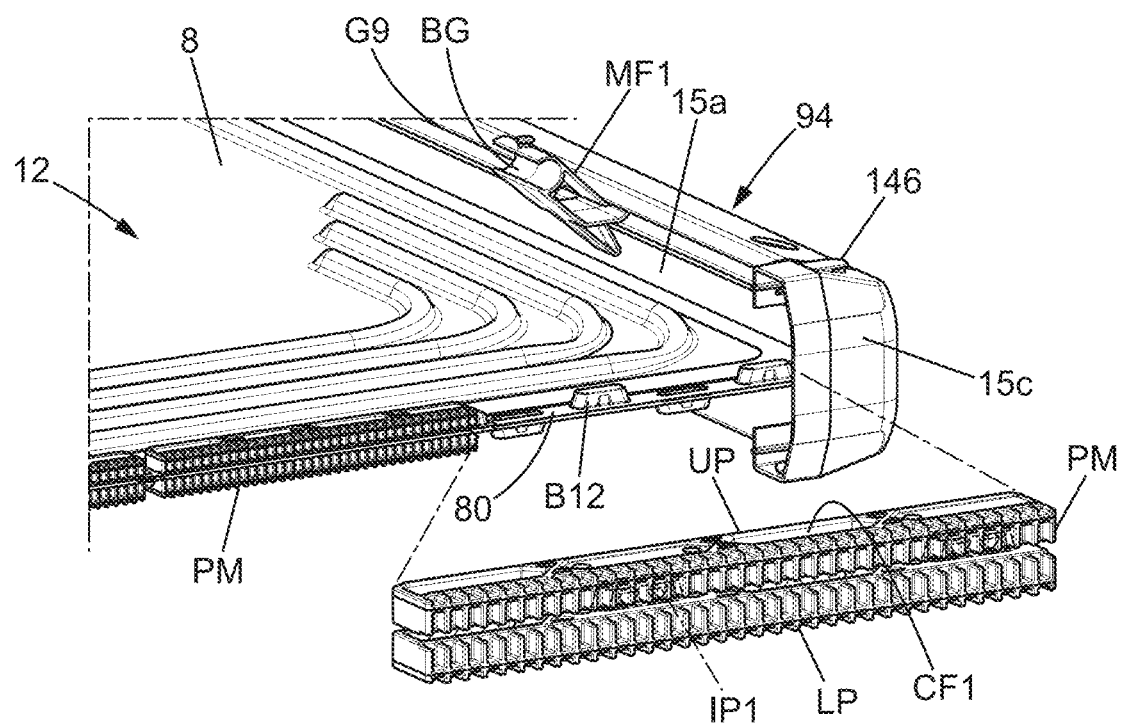
FIG. 4C is a detail view of a freeze/thaw system such as shown in FIG. 4A, illustrating an optional way to have lower and upper parts of a positioning member coupled to a region of the peripheral margin, here a transverse region, without additional fastening pieces.

The positioning members PM, PM' may be adapted to cover the boss portions B12, B12' such as illustrated in FIGS. 2A-2B and 4C or similar embossments. For instance, the positioning members may include several cavities each housing a respective pair of boss portions B12, B12' as in the example shown in FIGS. 4C-4G in particular. With such arrangement, there is no need for aperture or through-hole in the margin portions 8a, 8b of the plates (only one hole may be provided for the at least one port 24, at a front end of the protecting body).

Typically, the frame 15 may house the margin portions 8a, 8b sandwiched by a plurality of discontinuous positioning members PM. Along Z direction (see FIGS. 1 and 4A-4B), the depth of each hollow delimited by a boss portion B12 or B12' (such depth defining a stroke for disengagement between the complementary boss portions B12 and B12') may be superior to maximum spacing, measured along Z direction, between the frame 15 and any one of the positioning members PM. In such option, the frame 15 thus extends above and below each of the positioning members PM, PM' and prevents accidental disassembling of the respective pairs of boss portions B12, B12', which are parts of the attachment system 18. With such configuration, mounting and dismounting of the positioning members PM, PM' can be easy, with quick mounting performed after obtaining the assembled configuration of the protecting body 12, 112, 212.

FIGS. 4A-4D, 4F and 12A-12B illustrate a frame 15 having profiles 91, 92, 93, 94 each provided with one or more elongated cavities. Each cavity CP is delimited vertically between a lower section HP1, preferably formed by a horizontal wall, and a lower section HP2, preferably formed by a horizontal wall. The cavity CP is also delimited between an inner opened section 15a and an outer section 15b that may form an outer surface of the frame 15.

The outer section 15b may form a part of the side wall of the frame 15, which is here a rectangular side wall. The four elongated profiles 91, 92, 93, 94 and optional corner sections 15c for interconnecting two adjacent of the elongated profiles may form the outer side wall of the frame 15, thus defining an outer circumference (here a continuous circumference) of the frame 15.

Here, each profile 91, 92, 93, 94 has or comprises a C-shape section, with the opening of the inner open side, at the section 15a, delimited between two vertically spaced abutment members BS1, BS2. Each abutment member is here a continuous member elongated along length of the corresponding profile. But in variants, the abutment members BS1, BS2 may be divided into separated abutment regions or constructed in any suitable manner, without interfering with the protecting body reference plane P. In embodiments of FIGS. 4A and 12A-12B, the profiles have additional cavities above and/or below the elongated cavities CP, so that height of the profiles 91, 92, 93, 94 may be much higher that height of the cavities CP, for instance at least twice higher. The positioning members PM, PM' can be compact in height to be accommodated in such cavities CP, which may be less high than their radial extension (transverse extension perpendicular to axis X1, for the longer profiles 93, 94). Length of each positioning member PM, PM' may be longer, preferably at least three times longer, than any other size of the positioning members PM, PM'.

Figure 11B:
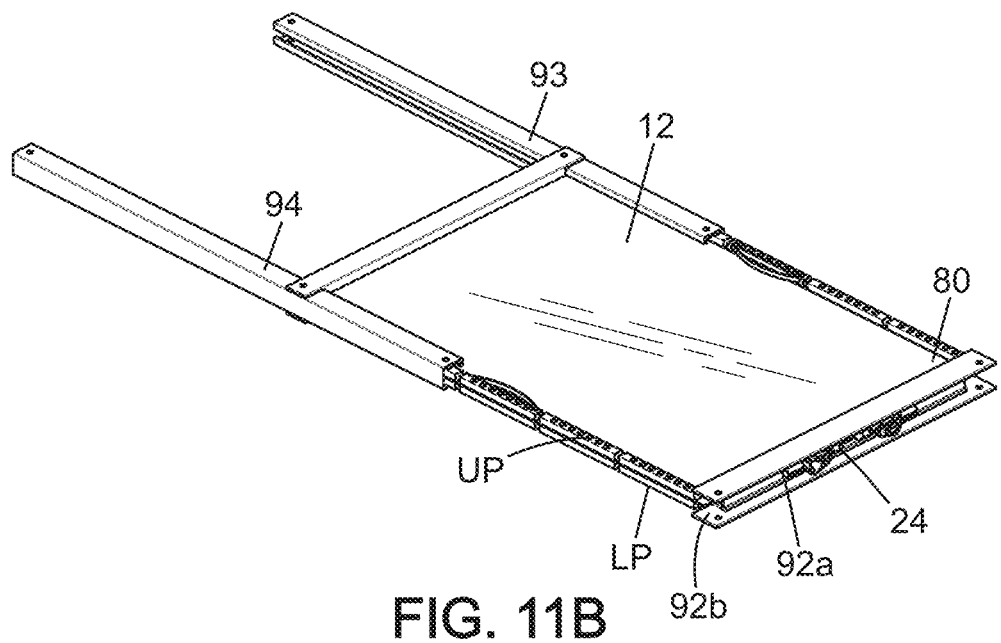
Figure 11C:
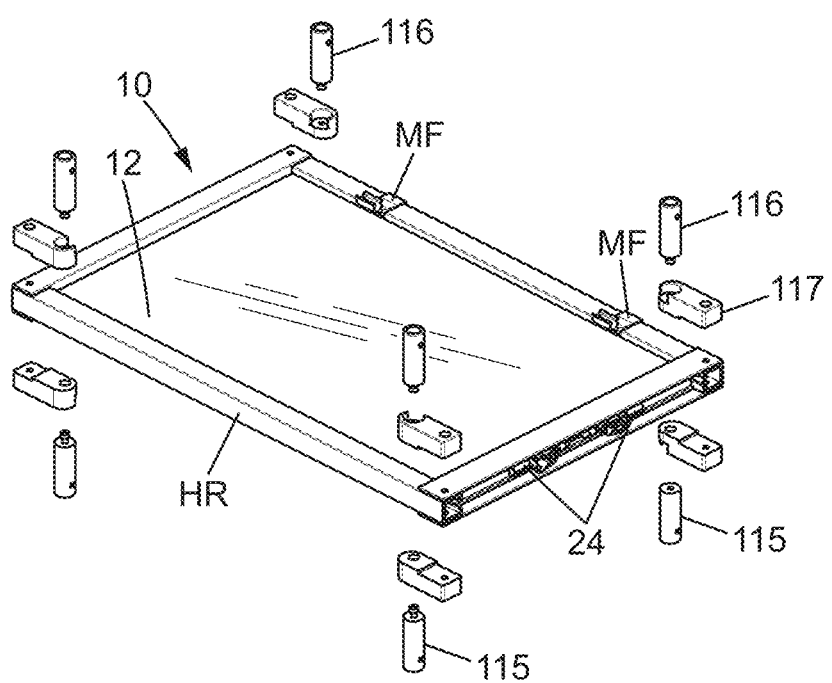
Figure 12A:
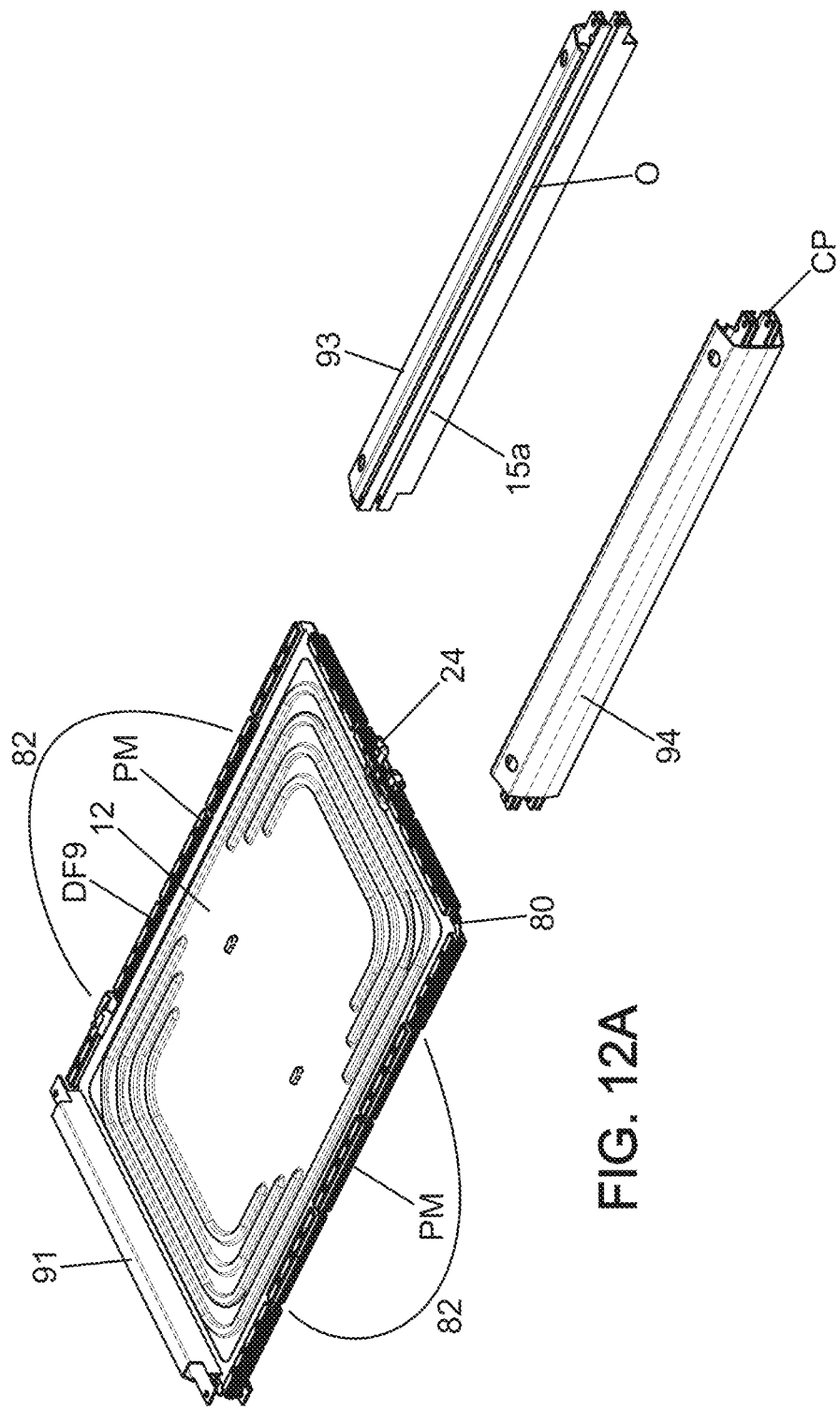
FIGS. 12A and 12B show respective states of the mounting of a holding and retaining assembly, here forming a rectangular frame, for holding the storage unit while allowing a controlled shrinking of the protecting body.

Here, as illustrated in FIGS. 11A and 11B or 12A in particular, the positioning members PM may be removably fastened to the peripheral margin 80, around the covering portion 8. Then, the positioning members PM disposed on the rear side (at the opposite from the at least on port 24 here) and the positioning members PM disposed on the two margin portions 8a, 8b are inserted in corresponding cavities CP of the profiles 91, 93, 94.

After mounting the positioning members PM; PM', the first profile 91 may be positioned to accommodate the rear margin portion of the protecting body 12, by a sliding displacement. Then, the positioning members PM at the two margin portions 8a, 8b are also received in elongated cavities CP by sliding insertion along a direction parallel to the long side of the profile 93, 94 in which they are housed. The respective parts LP and UP or any suitable piece of the positioning members PM may thus be inserted at the rear of abutment members BS1, BS2 and remain at the rear of the abutment members BS1, BS2 in assembled configuration of the frame 15 around the protecting body 12, 112, 212. In other words, each of the abutment members BS1, BS2 may be configured to separate the hollow space (for the pouch 2) from a cavity CP where each positioning member PM can be housed.

Figure 12B:
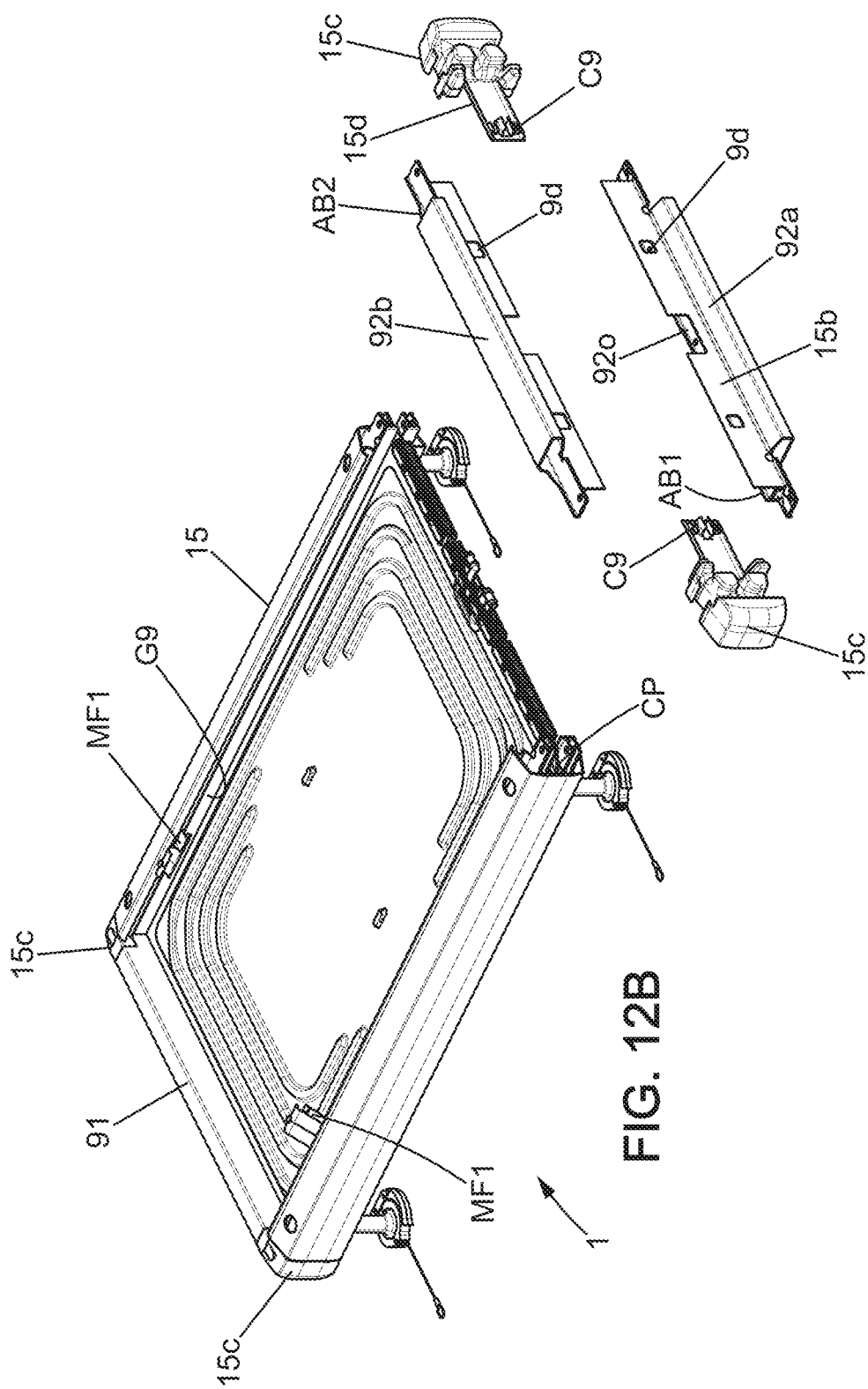

Corner sections 15c may be used as illustrated in embodiment of FIGS. 12A-12B. At least two corner sections 15c may be fastened to the transverse profile 91 (which is here a rear profile) before or after placing the longer profiles 93, 94. The positioning members PM, PM', may be arranged outside the corner sections 15c.

Regarding the positioning members PM, PM' received in the last profile 92 (the last to be assembled, here the front profile 92), FIGS. 4F, 6A and 12B show that a specific positioning member PM' is modified in its middle part to be deprived from insert portions IP1 or cavities CF1 for receiving boss portions B12. Indeed, along such middle part, the protecting body 12 has an opening 80a in a narrow region adjacent to the positioning member PM' and ports 24 of the pouch 2 extend longitudinally away from the covering portion 8 of the protecting body 12, across such opening 80a and across such middle part, through the passage openings OP1, OP2 shown in FIG. 4E.

Besides, all or part of the profiles may be obtained by assembling at least two profiled pieces: For instance, FIG. 12B shows two pieces 92a, 92b that are superimposed to delimit the cavity CP for receiving the positioning members PM and the positioning member PM' (which is here a central positioning member intersected by the longitudinal axis X1 of the protecting body 12). The two pieces 92a, 92b are assembled to form the profile 92 of the frame 15 (profile 92 as shown in FIG. 4A). The inner section 15a of the profile 91 composed of the pieces 92a, 92b may include an innermost wall of the piece 92a and an innermost wall of the piece 92b. The outer section 15b may be formed of a simple wall or a double wall, optionally provided with window(s) 9d for passage of clamp members C9. Each clamp member C9 can be used for holding a tubular portion of the hose T connected to one of the ports 24. Referring to FIGS. 11A-11C and 6A-6D, each longitudinal supporting part, typically under the form of a profile 93, 94 or similar piece, delimits one or more housings and is assembled with at least one adjacent supporting part (for instance two transverse supporting parts), also possibly under the form of a profile 91, 92. An annular housing may be included in the frame 15, when the profiles 91, 92, 93, 94 are assembled, possibly using lower feet 115 and/or upper feet 116 for supporting another frame 15 (see also FIG. 10). For instance, the two profiles 93, 94 respectively define a first housing and a second housing, in which the sliders are mounted.

Here, it can be seen that the sliders may comprise:
first sliders fitted in at least one cavity CP delimited by the first housing; and
second sliders fitted in at least one cavity CP delimited by the second housing.

Figure 8:
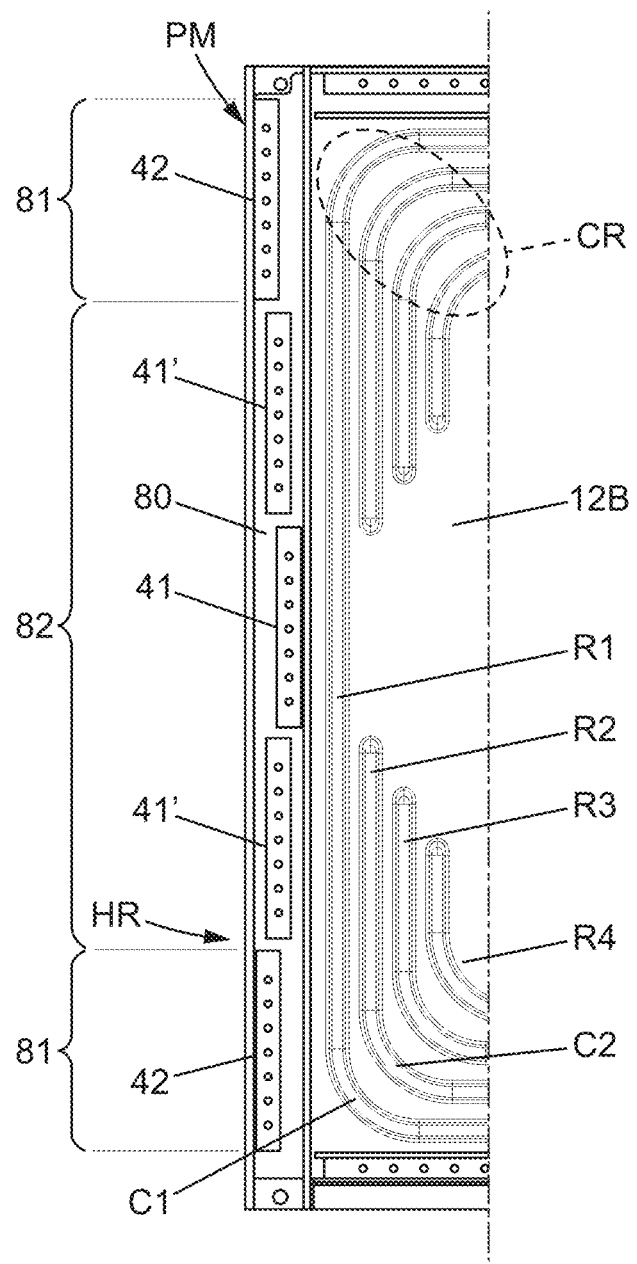
FIG. 8 illustrates a detail of an exemplary distribution of positioning members provided for holding/maintaining a same longitudinal side of the peripheral margin of the protecting body, allowing limiting bulge effect in a middle region of the storage unit in filled state of the flexible pouch.

Referring to FIGS. 8 and 11A, it can be seen that the sliders in the first and second housings will act as stoppers, more particularly either early stoppers 41 if mounted in a inwardly shifted manner on the peripheral margin 80, or late stoppers 41', 42 engaging abutment members BS1, BS2 at a later stage during filling of a pouch 2. The front surface BS of the early stoppers may possibly be already engaged, for a non-filled state of the pouch 2, onto one or more of the abutment members or rims BS1, BS2 provided in the frame 15, here in a middle region MR as in the option of FIG. 3.

Referring to FIG. 11A, each transverse supporting part, here formed as a profile 91 or 92, is configured for housing additional sliders, at least a part of which is acting as early stoppers. The front surface BS' of the early stoppers (orientated toward the pouch 2) may possibly be already engaged, for a non-filled state of the pouch 2, onto one or more of the abutment surfaces provided in the frame 15, here in transverse profiles 91, 92 or similar transverse supporting parts of the frame 15.

In the illustrated embodiments, all or part of the positioning members PM are configured to slide and thus form sliders able to be displaced inwardly with increasing filling level of the pouch 2. A first group of these positioning members PM are distributed longitudinally in the frame long sides, while a second group of the positioning members PM are placed along transverse areas of the peripheral margin 80 and distributed in the frame short sides. The sliders housed in the profiles 91, 92 or mounted on similar transverse supporting parts are each slidably mounted, in order to be movable along direction of the longitudinal axis X1.

The frame 15 has here a rectangular shape thanks to the two longitudinal supporting parts and the transverse supporting parts. It is thus understood that the frame 15 comprises abutment surfaces included and distributed in the two longitudinal supporting parts and in at least one of the transverse supporting parts.

Tubing Holder

Referring to FIG. 6A, one or two hoses or tubes T are typically connected to a front edge of the flexible pouch 2. A rear edge of the flexible pouch 2, at a longitudinal end opposite to the front longitudinal edge, may extend substantially parallel to the front edge. While each tube T may be bent and have a length superior to length of the longitudinal sides LS1, LS2 of the pouch 2, any size of hose/tube may be used. Each tube T may be maintained substantially parallel to the protecting body reference plane P, by attachment to a tubing holder provided in or attached to the frame 15 of the assembly HR.

Each hose/tube T is provided with a connector 17 for fluid connection, typically a connection to another biopharmaceutical device. The connector 17 thus makes it possible to fluidly connect the flexible pouch 2 to another element, for example a tank. In storage position of the tube (s) by use of the fixation means MF1, MF2, each connector 17 may be located between the longitudinal rear side 120*b* of the protecting body 12 and the middle region MR.

Referring to FIG. 4A, one or more of the elongated profiles, here the profile 94, may be provided with one or more fixation means MF1, MF2 for supporting at least one tube T that is connected to the port 24 or included in the pouch 2 as an extension defining the port 24. The tubing holder, including the fixation means MF1, MF2, may be distributed at least two spaced locations along a side of the frame 15, in a peripheral area of the system 1.

In an exemplary embodiment, the corner sections 15*c* have each a transverse extension 15*d*, formed as an internal part, adapted to be inserted inside the profile 92 provided with the opening 92*o* for the port(s) 24. Such extensions 15*d* extend linearly from a corner section external part toward the opening 92*o* and include the clamp members C9 that are formed as respective brackets, for holding a hose/tube T. Each clamp member C9 may be disposed between the port 24 and an external part of the front corner sections 15*c*. Each clamp member C9 is protruding outwardly from the outer section 15*b* through the corresponding window 9*d* formed in the outer section 15 of the profile 92. Referring to FIGS. 4F, 4G and 12B, the profile 92 here includes two parts 92*a*, 92*b* having an overlapping region for their outer wall, which form the outer section 15*b*. The extensions 15*d* may extend along such outer section 15*b*, to also delimit a rear part of the elongated cavity CP of the front profile 92.

Each bracket of a clamp member C9 has two flexible branches that define spacing suitable for hose insertion, so that the clamp members C9 can be used for holding a tubular portion of the hose T connected to one of the ports 24.

More generally, the frame 15 may be provided with clamp members C9 and/or grooves G9 for holding one or two hoses/tubes T that are connected to the pouch 2 via the port(s) 24, thus forming a tubing holder. Such tubing holder has holding parts distributed on at least two or three profiles 92, 93, 94 and optionally one or two corner sections 15*c*. Here, one or two profiles that are arranged perpendicularly to the front profile 92 include a part of such holding means, for holding the hoses T, above the protecting body 12 in preferred options. Depending on ease at accessing the top or bottom of the protecting body, the tubing holder may also extend below the protecting body 12 in some variants, using a groove G9 arranged below the protecting reference plane P.

It is understood that the tubing holder is arranged entirely outside the cavities CP, in order to not interfere with the peripheral margin 80, thus not interfering with liberty of motion of some of the positioning members PM, PM'. When groove G9 is provided in the longer profiles 92, 94, the groove G9 may be substantially as long as the flexible pouch 2 and/or as long as the space delimited between the opposite transverse profiles 91, 92. This allows flexibility in positioning fixation means MF1 provided with an anchoring piece using the groove G9.

In a first option, fixation means MF1 of the tubing holder include one or more anchoring pieces having an anchoring relief 160 having a complementary in shape with respect to the receiving groove G9 of one of the longer profiles 93, 94. Each anchoring piece may also be provided with an abutment end 162 in contact with a surface (here a substantially vertical surface) of the inner section 15*a*. The anchoring piece may extend upwardly from a joint part joining anchoring relief 160 and the abutment end 162, such joint part being optionally a hollow part or recessed part to improve deformation of the anchoring relief that may be clipped in the groove G9. The anchoring piece further includes, at an upper end thereof, the fastening member 147 for holding the sample unit SU parallel to the frame 15, thus substantially parallel to the reference plane P in illustrated embodiments. The single piece construction of such fixation means MF1 simplifies the mounting steps. It may also be of interest for receiving more than one component, especially when also having a sample unit SU supported by the fixation means MF1 whose positioning is easily adjustable in length along a profile 93 or 94.

It can be seen that the sample unit SU is attached above the two longer profiles 93, 94, at a distance from the rear corner section 15*c*, while being also attached at one or more fastening members 146 arranged at the rear end of the frame 15. In some options, such additional fastening members may be formed near a protecting body rear end, typically outside the peripheral margin 80.

Referring to option illustrated in FIGS. 4C and 6E, the hose/tube T may be simultaneously be received and/or guided in:

the groove G9 (in a part of the groove G9 away from the rear profile 91 and close to the front profile 92), and the blocking groove BG of the anchoring piece.

This of interest to have a compact arrangement of the whole system 1, with the outer circumference of the system only delimited by the profiles, here by the outer sections 15*b* of the frame 15, efficiently acting as a protection for the pouch 2, which is already sandwiched between the two plates 12A, 12B.

The fixation means MF1 are easily removable, as a simple rotation of the anchoring piece may be sufficient for unclipping this piece from the groove G9. There non need for tool for removing the hose/tube T from the guiding groove G9 as the tube end is already available/outside thus groove G9 by being clipped in the blocking groove BG which is very short as compared to the elongated groove G9.

Referring to the other option illustrated in FIGS. 10 and 11C, the fixation means MF1, MF2 may comprise at least one fixing element 110 that can be snapped on the frame 15, here by engaging on the outer part of the rail-like profile of the frame 15. For instance, the fixing element 110 is a bracket that partly surrounds a receiving profile, which may be one of the longitudinal profiles 93, 94 or another profile 91, 92. Some holes 94a in the profiles (see FIG. 6C) may receive a pin or similar retaining inner protruding part of the bracket, for instance for an anti-sliding effect.

The bracket may be resiliently deformable, allowing removal of the fixing element 110 relative to the frame 15, for instance by spacing the arms of the bracket further away. The bracket may also be hinged in some options. Accordingly, the tubing holder formed by the fixation means MF1, MF2 may be removed once line used (inlet line not useful anymore after filling line disconnected).

The fixing element 110 is here C-shaped or U-shaped in a section view, thus forming a bracket. The bracket delimits an interior space or recess for accommodating a portion of the profile 94. Referring to FIG. 10 or FIG. 6E, the tube T may be a filling line connected to the pouch 2, for the purpose of the filling operation. For instance, the tube T is received and held/positioned by the fixation means MF1, MF2, while remaining connected (permanent connection) to the pouch 2 via a connector. Another connector, which is an aseptic connector, may be provided with two complementary parts Cli at the other end of the tube (at the opposite from the permanent connection). This allows an aseptic disconnection of tubing in biopharmaceutical manufacturing processes.

The fixing element 110 may also comprise a clamping part 113, forming a receiving cavity delimited by a concave inner surface. A portion of the tubing outer wall, which may be cylindrical, can be inserted and fitted in this receiving cavity (the same manner as in the blocking groove BG). The portion of the tube T received in one or two cavities of the fixing element(s) 110 or in the blocking groove BG, respectively, may extend entirely above the plane XY when the protecting body and the pouch 2 extend horizontally.

The more the flexible tube T is away from the periphery of the system 1, the lower is risk for accidentally handling and disconnecting this hose or tube T, during transportation steps for instance. But this tube T remains here easily available for operators.

The tubing holder may be an assembly for holding two tubes T, in order to be symmetrically arranged with respect to the longitudinal direction X (i.e. pouch longitudinal axis A). Each symmetrical part is able to hold one hose/tube T.

While FIGS. 4A, 6A and 10 show each a solution for horizontal storage, it is understood that the pouch 2 can also be stored vertically or along any suitable direction, thanks to a storage unit 10. A sliding structure may be used for having the protected pouch (in frozen state) carried by an annular frame or similar holding means that can extend vertically for storage purposes.

Filling of the Pouch

Several flexible pouches 2 may be filled and protected in systems 1. A shelf may be formed with several superimposed systems 1, as shown in FIG. 10. The flexible pouches 2 in these systems 1 can be frozen, thawed, filled or emptied simultaneously when they are stored on such kind of shell device. When the flexible pouches 2 are stored, the biopharmaceutical fluid/composition Q can be frozen or thawed. When the flexible pouches 2 are shipped, most often, the biopharmaceutical composition Q is frozen even if the biopharmaceutical fluid can as well be thawed.

The flexible pouch 2 can inflate during filling operation, which means that the circumference of two main walls W1, W2 as considered in the pouch plane (corresponding to the protecting body reference plane P) is decreasing due to inward movement, also known as shrink stroke, of the different sides. Here, in horizontal configuration of the system 1 as illustrated in FIG. 4A or 6A, four pouch sides can be displaced inwardly due to the vertical expansion (along Z-axis).

Referring to FIGS. 1-3, the pouch expansion is limited and controlled by the protecting body 12, 112, due to lower flexibility of the material of the two plates 12A, 12B, optionally provided with outer ribs. The protecting body 12, 112, 212 is made of a freeze resistant polyester or copolyester material that is not brittle at about 25° F. or −4° C. This material is for instance PET or a robust copolyester of TRITAN™ type.

Referring to FIGS. 3, 5A and 7A-7B, the supporting structure, typically under the form of frame 15, may receive and guide the positioning members PM, PM', so that, during filling operation, the system 1 is suitable for shrink management of the protecting body 12, 112, 212 containing the pouch 2.

Protecting body shrink is managed through the positioning members PM, PM' acting as stoppers and the rigid covering portions, here formed as elongated profiles 91, 92, 93, 94 that are maintained/fastened in a frame structure. Four corners are provided in the frame 15, possibly using specific front and rear corner sections 15 made separate from the profiles 91, 92, 93, 94, to ensure that:

the profiles 93, 94 remain parallel and cannot move relative to the longitudinal axis X1; and the profiles 91, 92 remain perpendicular to the longitudinal axis X1.

Since the stopper-like positioning members PM are attached to the edges at the peripheral margin 80 and also encapsulated or retained in the annular housing included in the frame 15, adding a gap between the sliding positioning members PM and the abutment surface AB1, AB2 will allow these sliding positioning members PM to move in one direction, more precisely:

in X direction for the stoppers/positioning members PM located on the long side of the peripheral margin 80;

in Y direction for each of the stoppers/positioning members PM, PM' located on a short side of the peripheral margin 80.

This two-axis freedom of motions will allow the protecting body 12, 112, 212 to shrink in the protecting body reference plane P and to expand vertically in order to have the pouch 2 filled at the required volume.

Referring to FIG. 11A or FIGS. 4D, 4G and 12A, it is illustrated positioning members PM that are constructed identically, for instance using a lower part LP and an upper part UP that are mutually fastened (respectively below and above the peripheral margin 80). Due to a difference in position or thanks to mounting of an abutment contact part, some of the positioning members PM can be then differentiated, and provided with a specific front surfaces BS, possibly distributed to be integral with the lower part LP and the upper part UP of a given positioning member PM differentiated as an early stopper.

Figure 4D:
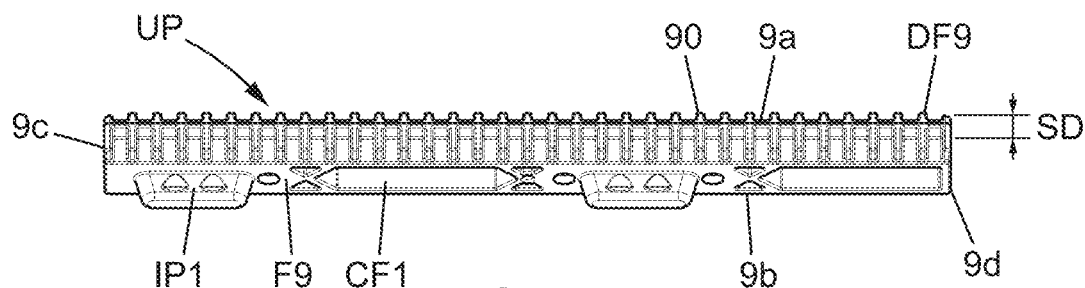
FIG. 4D shows an unsymmetrical piece able to provide a retaining function of the protecting body when coupled to reliefs of the peripheral margin.
Figure 4E:
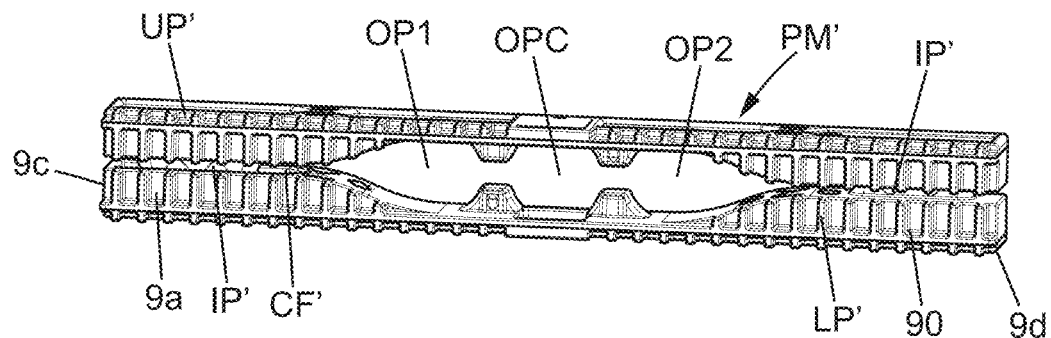
FIG. 4E shows an additional positioning member configured to extend around tubular parts of ports provided in the flexible pouch, when being coupled to reliefs of the protecting body peripheral margin.
Figure 4F:
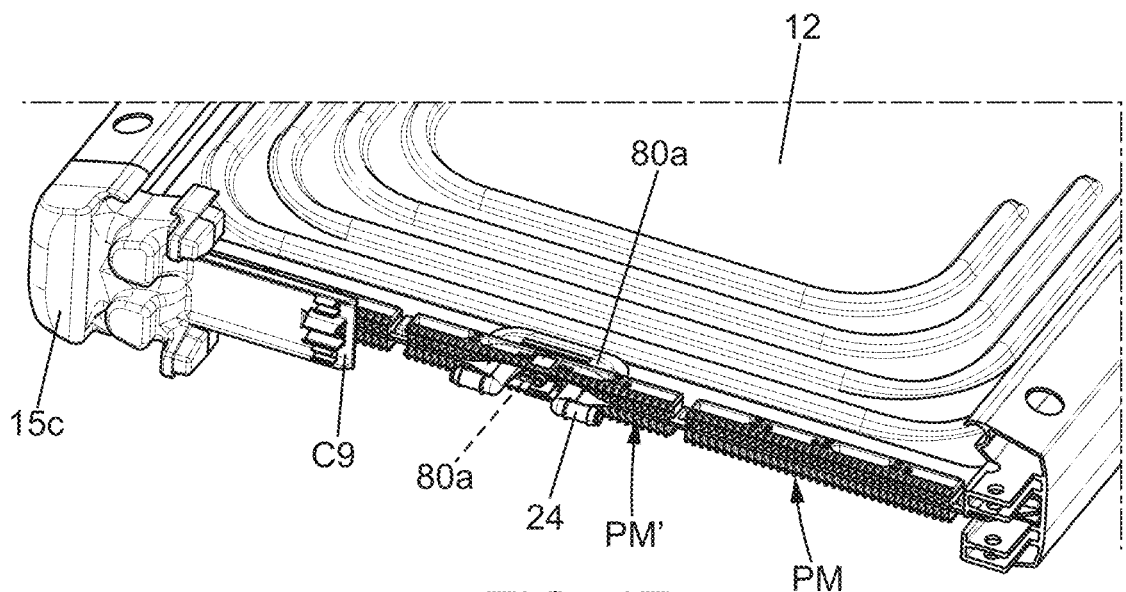
FIG. 4F illustrates a front part of the system of FIG. 4A, without a front part of the frame, in order to show positioning members coupled to a peripheral margin front portion.
Figure 4G:
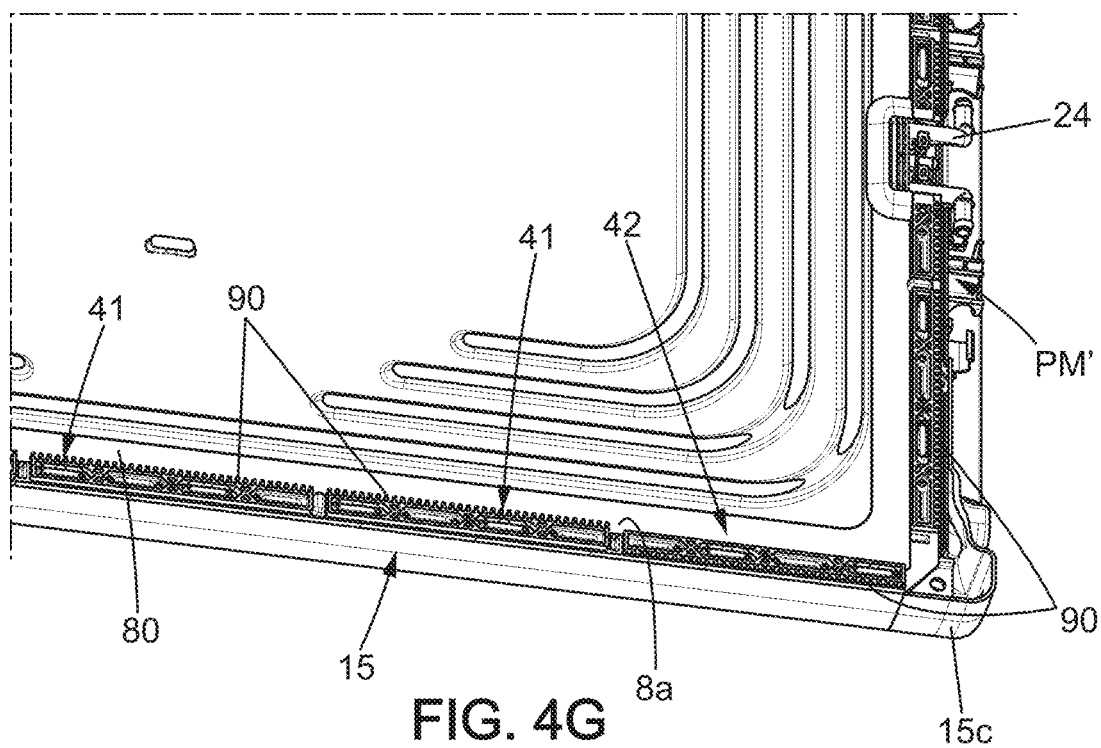
FIG. 4G is top section view of a detail of the system of FIG. 4A but in non-filled state of the pouch and with some of the internal positioning members adjusted in a modified configuration as compares to the other positioning members, in order to selectively limit plate displacement and shrinking in a middle region of the protecting body.

FIG. 4D shows a half of a positioning member PM, which may be the upper part shown in FIG. 4C. Here, the positioning member PM is composed of two identical halves: one forming the upper part UP, the other one forming the lower part LP. Each positioning member PM is elongated and extends between two opposite ends 9c, 9d. The positioning member PM has two opposite sides 9a, 9b generally parallel to the protecting body 12 in assembled configuration (here horizontal faces), one of these sides corresponding to or including a face F9:

provided with plug parts (IP1, CF1), and which is facing toward the peripheral margin 80 to have the plug parts (IP1, CF1) that match (her match exactly) the profile of several elements, here four relief elements, of the fastening system 18 included in the margin 80.

Besides, the positioning member PM has two parallel elongated faces, which extend perpendicular to the reference plane P in assembled state. The interior face of the positioning member PM is one of these two parallel elongated faces and is suitable for being engaged on the one or more abutment surfaces AB1, AB2 provided in the frame structure, such engagement being function of the filling level of the pouch 2 sandwiched by the plates 12A, 12B.

In some options, the positioning member PM, PM' have one or two parts LP, UP, LP', UP' that are able to be plugged on the peripheral margin 80. Each part has an interior face facing toward an abutment surface AB1 or AB2 and an exterior face. With respect to the plug parts provided in the contact face in contact with the protecting body 12, one amongst the interior face and the exterior face is a face DF9 more offset than the other face, such offset along a radial direction (corresponding to the shrink direction) being of interest for having a part of the positioning members PM, PM' able to slide more than other positioning members. This allows shrink management, for instance for having the effect schematically illustrated in FIGS. 9A-9B (higher containment level in a middle area of the protecting body 12, thus minimizing a bulge size in a middle section MS of the pouch 2).

Referring to FIG. 4G, it can be seen that the unsymmetrical piece structure of the parts UP, LP may be advantageous to have efficient plugging or similar mounting on the peripheral margin 80, and ability to position the positioning members PM more or less close to the inner section 15 (where the abutments surfaces AB1, AB2 are formed) of the frame 15. As compared to the assembling of FIG. 8 where the parts of the positioning members, typically having an attachment function for securing the plate 12A to the plate 12B, have to be disposed at irregular predetermined positions, configuration shown with the offset face DF9 also enables having a peripheral margin 80 without throughholes and/or with low flexibility for changing disposition of the positioning members PM.

While the offset face DF9 is here provided with reliefs or ribbed portions 90, any other surface may be obtained for having the face DF9 more distant from the plugging area that the opposite face. The offset or shift distance SD in such asymmetric pieces may be superior or equal to 2 or 3 mm, possibly about 6 or 7 mm (typically less than 10 mm).

In the embodiment of FIGS. 4F-4G, near the corner sections 15c, the respective offset faces DF9 are exterior faces in the lower and upper parts LP, UP. In contrast, at mid-distance between a rear corner section and a front corner section along a same frame side, at least one or two positioning members are in a different position, 180° rotated around Z direction as compared to the other positioning members PM mounted at same margin portion 8a or 8b. Such configuration may be obtained in the two margin portions 8a, 8b, with only intermediate parts 82 of the protecting body 12 being plugged by positioning members PM whose interior face is an offset face DF9 for forming an early stopper during pouch filling operation.

Referring to FIG. 4E, the positioning member PM' surrounding a part of the port(s) 24 may also be elongated, preferably for having substantially same length as the positioning members PM in an exemplary embodiment. This specific centrally open positioning member PM' also has halves, preferably identical halves, each extending between two opposite ends 9c, 9d and provided with a offset face having here reliefs 90, allowing a greater shrink stroke (in a profile cavity CP) when the offset face is facing radially outwards, as compared to some of the positioning members PM that have the offset face DF9 facing radially inwards.

While the stoppers may be distributed symmetrically as far the peripheral margin long sides are concerned, distribution in the short sides may be either symmetrical, or non-symmetrical in the short sides. FIG. 11A illustrates an option with three front surfaces BS' distributed in three corresponding positioning members PM arranged in two opposite short sides of the peripheral margin 80. While, inside the front profile 92, two early stoppers may be formed near the corner regions CR and away from a median region where the opening 80a is provided for the port(s) 24, other distributions are available.

Figure 5A:
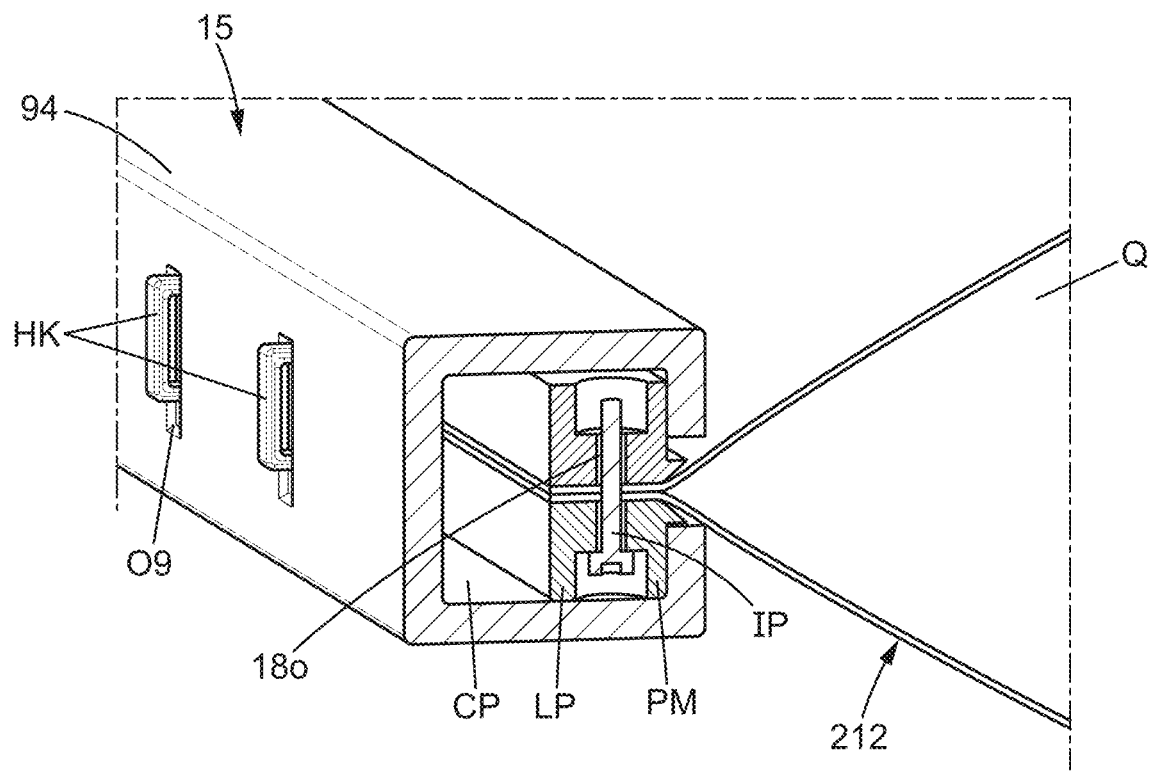
FIG. 5A is a perspective view illustrating an exemplary integration of a positioning member formed as a slider that is movable inwardly relative to a stationary frame part in a filled state of the pouch sandwiched by the plates of the protecting body.
Figure 5B:
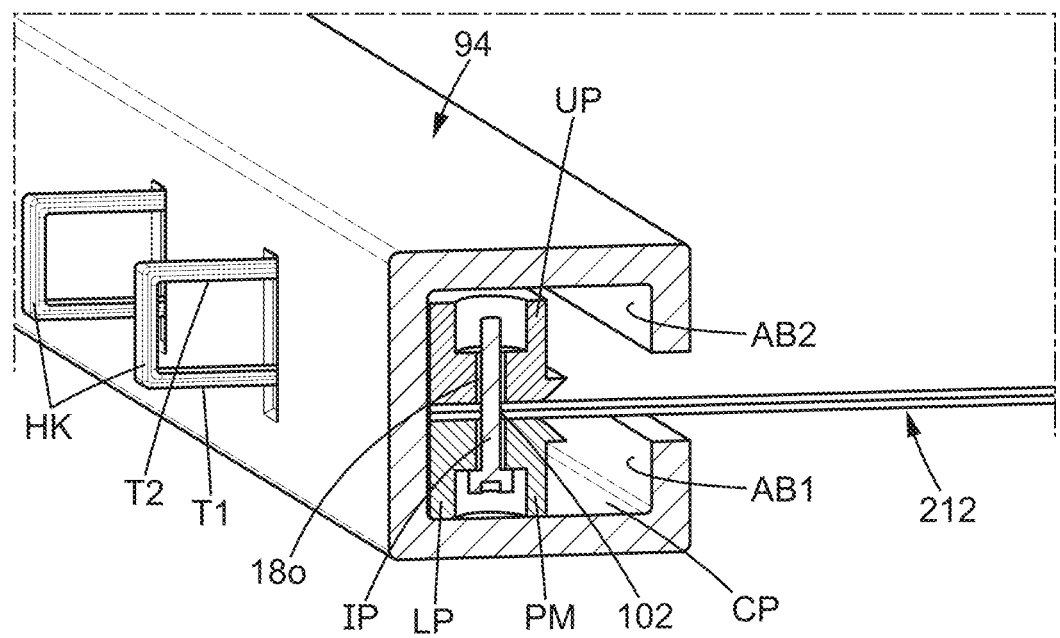
FIG. 5B is a perspective view similar to FIG. 5A, illustrating a first position of a positioning member formed as a slider, which may be a default-position for a non-filled state of the pouch sandwiched by the protecting body, such first position being obtained either before a filling operation, or after a draining operation of the content of the pouch.

In some variants, the attachment device or system 18 comprises one or more cross members that are configured to maintain the positioning members PM in an assembled state. Such cross members may include an insert piece IP (FIG. 5A) and associated fastening lock (for instance a mechanical lock such as nut, bolt or the like). Referring to FIGS. 5A-5B, such cross members are engaged with a retaining effect through the hole 18o that matches with a pair of slots or apertures 102 provided in the plates 12A, 12B.

The cross members are part of attachment means, which may be in a locking state. In the locking state, the cross members cannot move or slide along Z-direction through the protecting body 12, 112, 212, in order to prevent vertical separation of the parts UP, LP of the positioning members PM. Referring to FIG. 7A, the upper part UP and the lower part LP are sandwiching the peripheral margin 80, typically in an area that is outside the sandwiching of the pouch 2. FIG. 7A illustrates initial position of the positioning members PM, in empty state of the pouch 2. A Gap is provided between each of the parts UP, LP and the inner side or inner section 15a of the corresponding receiving profile, so that shrink is allowed. A gap between the exterior face of the positioning member PM and the outer section 15b may be provided here. When the protrusions or reliefs 90 are facing externally (which is the case for members PM arrange away from a middle part of the respective margin portions 8a, 8b for instance), there is initially a higher gap between the inner section 15a and the interior face of the positioning member PM, thus allowing a greater sliding stroke and a greater angle between the sheets 21, 22 of the pouch 2.

Referring to FIG. 7B, such higher sliding stroke may be also obtained with use of reliefs 90' that just pass through the inner section opening (elongated opening O). The shift distance SD' thus may be obtained without having the reliefs 90' abutting against an abutment surface AB1, AB2. More generally, the way unsymmetrical features are integrated in the positioning members are not limited to illustrated examples.

Referring to FIG. 7B, it can be seen the biopharmaceutical composition Q has been introduced in the flexible pouch 2 and each of the positioning members PM can be displaced inwardly, possibly in a final position, in which the positioning member PM is abutting inwardly against abutment rims BS1, BS2 of the frame profile. Each of the parts UP and LP may include a front protruding portion or reliefs 90' that engage/extend through the elongated opening O of the profile, in a filled configuration of the pouch 2.

Each front protruding portion or reliefs 90, 90' of these parts UP, LP may have a slanted surface reaching the pressing face in contact with the protecting body 2, in order to form a V-like section groove GS (distributed on both sides of the body peripheral margin 80) that opens inwardly. This groove GS may guide the expansion of the protecting body near the peripheral margin 80, in order to prevent direct contact of the surfaces S, S' against the frame 15 (thus preventing any contact against any profile edge/surface). This of interest for protecting the protecting body material, as the profiles 91, 92, 93, 94 are typically in more rigid material, for instance steel, metal or rigid plastic.

Referring to FIG. 1, the two plates 12A, 12B are flexible enough to allow the protective body 12 to locally have a thickness, in or near a central area, which is greater than in a circumferential area. Thus, when the biopharmaceutical fluid is frozen, the containing region/receiving part 2r or useful part of the flexible pouch 2, i.e. inner region relative to the peripheral seal J, may be slightly curved. Hence, a dimension on the longitudinal direction X of the protecting body 12 slightly decreases. In this case, the biopharmaceutical fluid is slightly constrained by the two plates 12A, 12B.

Draining of the Pouch

Referring to FIG. 6D (see also FIG. 11A or 12A), the positioning members PM may be assembled in the whole periphery defined by the peripheral margin 80, so that more than 80% of the periphery of the peripheral margin 80 is covered with positioning members PM, PM'. Here, the spaces between the positioning members PM are small, for instance less than 5 cm or less than 5% of the length of the protecting body, possibly except at angles of the protecting body and/or at an opening 91a included in the profile 91 matching with the opening 80a.

With such arrangement, the useful volume contained by the protecting body under the covering portion 8 has limited deformation (non-significant wave shape deformation). Moreover, such sliding is performed during filing and during draining. After draining, the sliders/sliding positioning members PM, PM' can slide back with the protecting body recovering its maximal perimeter (i.e. initial perimeter), without interference due to the frame 15.

To prevent formation of undesirable waves or similar reliefs at the outer surfaces S, S', some sliders 41 are configured to allow a belt effect in the middle region MR, as it will be described below in more detail (see FIG. 9A for instance). After draining, absence of waves is advantageous since the plates 12A, 12B cannot get stuck with the frame 15 at the inner side openings: this minimizes the residual volume (hold-up volume) after draining operation.

Besides, in cases where the pouch 2 is not filled at its full capacity, for instance with 75 L for a 100 L pouch, draining optimization may be obtained in some options using biasing members BM, BM' that are acting for having appropriate tension of the plates 12A, 12B, thus preventing undesirable waves or similar pronounced irregularities/reliefs on the outer surfaces S, S'.

Referring to FIGS. 6B-6C, the biasing members BM, BM' are configured to exert a return action for displacing the sliders/sliding positioning members PM outwardly toward the first (initial) position which is a by-default-position in non-filled/emptied state of the pouch 2. FIG. 6B illustrates an example of a positioning member PM provided with a contact face or part made of foam material and/or silicone (possibly with lattices, or extruded silicone). This may be any suitable compressible material having a shape memory or a sufficient resiliency Such contact part, here at the front of the positioning member PM, pulls back the corresponding region of the peripheral margin 80.

When having positioning members provided with an upper part UP and a lower upper part LP separated from the upper part UP by the peripheral margin 80, the biasing member BM made of compressible material may be also be divided in two parts: an upper biasing part UBM and a lower biasing part LBM, each extending in cavity CP or similar interspace respectively between the front surface of the member part UP or the front surface of the member lower part LP and a abutment surface AB1, AB2.

The biasing member or similar piece tenses the plastic plates 12A, 12B to compress and maintain the pouch even if it is filled much below its capacity. This return force solution is typically used to:

maintain contact, as continuous as possible, between the pouch 2 and the plates 12A, 12B;
tense the plates 12A, 12B for pouch protection (by reducing freedom of motion of the pouch 2) after partial draining (aliquot) or when the pouch is under filled;
protect under filled pouch from eventual shocks between the stoppers/positioning members PM, PM' and the frame 15 caused by handling or shipping stresses.

Of course, filling of the pouch 2 still causes progressive deformation of the protecting body 12, 112, 212, in order to create (in the protecting body reference plane P) a pulling action to pull the sliders inwardly, the pulling action increasing with level of filling of the pouch 2 and being opposite to the return force/action of the biasing members BM, BM'.

In embodiment of FIG. 6C, the biasing member BM' also provides one or more contact parts in contact with the abutment surfaces AB1, AB2 in the second position, for a filled state of the pouch 2. In this example, a leaf spring or similar spring part is provided to tense the plastic plates 12A, 12b, in order to to compress and maintain the pouch 2. Each biasing member BM' is configured to exert a return action for displacing the sliders/sliding positioning members PM outwardly toward the first position in non-filled state of the pouch.

The biasing member BM' may optionally be provided with two branches 75a, 75b each forming a contact end against a corresponding abutment surface AB1, AB2, here above and below the margin portion 80. The biasing member BM' is possibly a single piece 75 forming a leaf spring. This biasing member BM' may have a fastening part, possibly not deformed during use, which is fastened to a positioning member PM via one or more insertion pin 78. The positioning member BM' may sandwich the associated positioning member PM in some options, for instance using a bracket as a fastening part, while one or more deformable parts 76 are provided as extensions attached to the bracket. Each deformable part may be spaced, partly or entirely, from the positioning member PM and protrudes forward relative to a positioning member front face.

Now referring to FIGS. 5A-5B, some hooks HK may be provided with a handle part for manipulating and pulling the positioning members PM (outwards). Here, the hooks HK are attached, directly or indirectly, to the positioning member, preferably at the opposite from the abutment surfaces AB1, AB2. These hooks HK will give access to the protecting body edges in order to allow the users to pull these edges manually, in order to drain the pouch 2 completely if needed.

Such solution may be provided with or without integration of biasing members BM, BM'.

More generally, the frame 15 of the system 1 may be provided with any suitable pull elements. In the illustrated embodiments, the pull elements include guiding members T1 that are displaceable transversely relative to the two longitudinal supporting parts and coupled to portions of the peripheral margin 80. Some windows O9 may be provided in at least one outer face of the frame 15, for having guiding members T1 of the pull members displaceable from cavities CP toward the outside of the frame. The pull elements are configured to pull all or part of the peripheral margin 80 outwardly, here from position shown in FIG. 5A to position shown in FIG. 5B, when the pull elements are displaced from a retracted position to an expanded position (position with operating parts of the pull members away from the frame 15, as illustrated in FIG. 5B).

Details of Exemplary Embodiments for Controlling Pouch Expansion

In embodiment of FIG. 8, the plate dimension reduction (as considered in XY plane) is obtained with a profile of shrink strokes, such reduction being adjusted to be different, depending on longitudinal positions of some positioning members PM that locally prevent or limit such dimension decrease, for a control of the shrink stroke.

Here, the positioning members PM (which are secured to the peripheral margin 80 as illustrated in FIGS. 7A-7B) are distributed longitudinally and some of them are configured to limit shrink stroke of the longitudinal sides of the protecting body by a stopping effect due to engagement of the positioning members PM against the interior surfaces of the abutment rims BS1, BS2.

All or parts of the positioning members PM are stoppers for providing strokes limitation between the stoppers 41, 41' 42 and the abutment surfaces AB1, AB2 included in the frame 15 of the holding and retaining assembly HR. Referring to FIGS. 8 and 9A, the stoppers 41, 41' arranged at or near a middle section MS of the pouch 2 are involved to create a belt effect. In some embodiments, such belt effect is separating two bellies or bulges B1, B2.

Figure 9A:
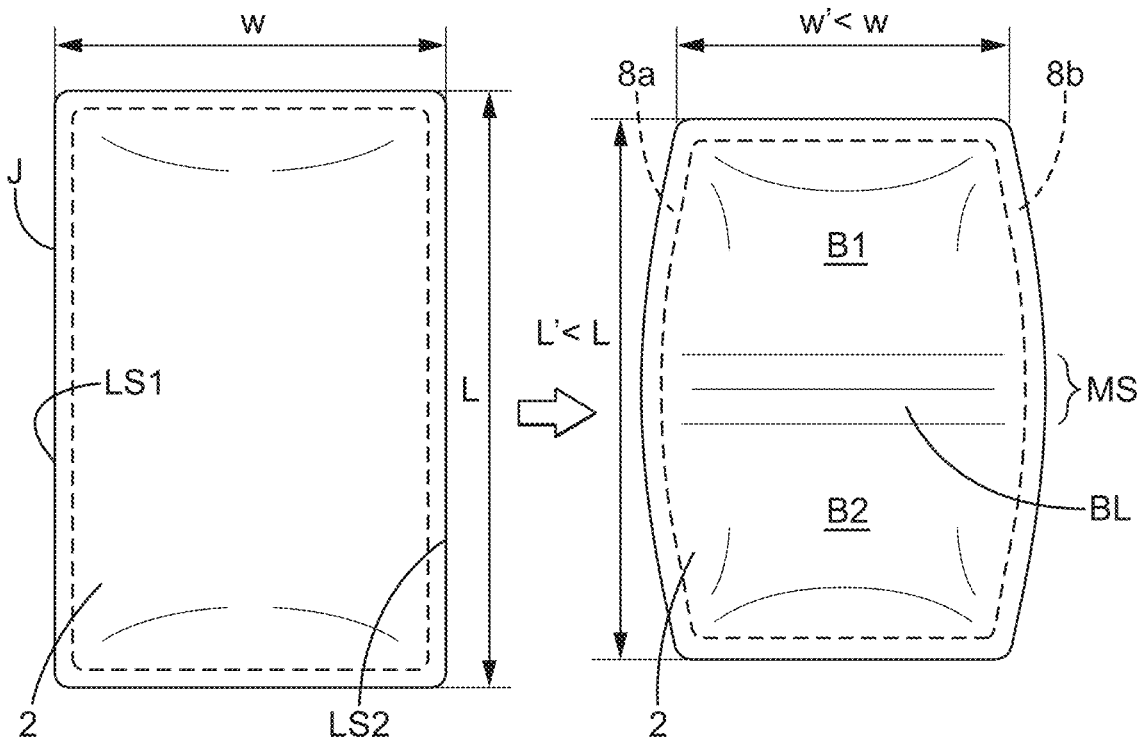
FIG. 9A is a top view of the flexible pouch filled with liquid inside the system of FIG. 8 without illustrating the protecting body and the positioning members.
Figure 9B:
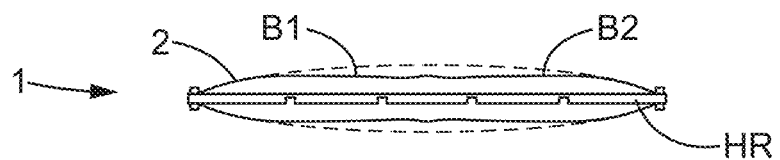
FIG. 9B is a schematic side view showing a frame-like holder and the flexible pouch filled with liquid inside the system of FIG. 6A or 8 without illustrating the protecting body and the positioning members.

Referring to FIGS. 8 and 9A-9B, the positioning members may act as stoppers 41 or 41' only in the two intermediate parts 82 of the protecting body 12. As a result, since stroke is allowed in regions closer to the corner regions CR, here in the end parts 81, the pouch 2 covered by the containment protecting body 12, 112 or 212 cannot form a single belly or bulge in the middle thereof.

Moreover, the optional ribs R1, R2, R2', R3, R4 prevent the plate outer surface S, S' from forming fold lines or hollows that limit good filling of the biopharmaceutical composition Q in the corner region. Such ribs, possibly with regions or portions of lower height (for instance only at the diagonal lines DL1, DL2 as guiding and accordion-like effect is already obtained along the four sides of the rectangular shaped protecting body 12, 112) may help in expanding the protecting body 12, 112 from the inside without creating hollows or inappropriate fold lines detrimental to filling at the corner regions CR.

It is understood that at a given level of filling, the pouch corners and protecting body corners can continue to move inwardly during filling operation, while the intermediate parts 82 are blocked by the stoppers 41, 41'. At the corner regions CR, shrink strokes are longer than in the middle and will allow storing at least the same liquid capacity than without the belly/bulge retention.

Still referring to FIG. 8, the stoppers 41, 41', 42 may be at predefined positions, in order to form positing members PM. Here, only the stoppers 41, 41' that are located away from the end sides 120a, 120b have a relatively closer distance to a median symmetry plane of the protecting body 12, as compared to distance for the stoppers 42. In such option shown in FIG. 8, such stoppers 41, 41', 42 follow displacement (shrinking) of the peripheral margin 80.

It could be observed that the positioning members PM of FIGS. 4D, 4F-4G and 12A may also include such stoppers, which correspond to configuration with the shift face DF9 facing inwardly, so that similar intermediate parts 82 can be provided with positioning members slightly more distant from the long edge of the plate, as it is the case in the example of FIG. 8. FIG. 4G also shows that first stoppers 41 are formed by the members that extend less outwardly along Y direction, while second stoppers 42 are formed by the other members PM, PM'.

During filling operation, as the stoppers 41, 41' provided in intermediate parts 82 of the longitudinal margin portions 8a, 8b are (initially) shifted inwardly due to arrangement of the attachment system 18 and/or due to a unsymmetrical disposition, and because the abutment surfaces AB1, AB2 are in alignment, parallel to the X direction, these stopper 41, 41' are in abutment state against the abutment surfaces AB1, AB2 well before the stoppers 42 adjacent to/facing a corresponding corner region CR. A belly retention effect at the middle of the protecting body 12, 112 is obtained.

In options, ribs R1, R2, R3, R4 are provided in the plates 12A, 12B, possibly with corner ribs C1, C2 having a decreasing height profile toward the intersection region with the diagonals DL1, DL2. In such kind of option, the retention effect (decreasing bulge effect in the middle region MR, near the center C) is completed by a regular expansion of the regions around the panels PP or PP1, PP2, preventing undesirable formation of pronounced fold lines.

Of course, FIG. 8 is only an exemplary embodiment for managing the shrink of the plates 12A, 12B. More generally, the protecting body 12 can be mounted to sandwich the flexible pouch 2 and may be received/hold in an interspace of any suitable holding and retaining assembly HR, which is rigid and delimits an outer circumference of the system 1. Depending on level of filling of the pouch 2 sandwiched by the plates 12A, 12B, the protecting body 12 may comprise one or more areas of maximum thickness. In order to accommodate this thickness variation, the holding and retaining assembly HR may be of annular shape.

The one or more bulges/bellies B1, B2 as illustrated in FIG. 9A-9B can be formed due to the expansion control and early stopping effect at the intermediate parts (thanks to the early blocking stopper 41 and/or 41' for instance), so that the middle section MS is much less moved as compared to complementary sections covered by parts of the protecting body 12 that are near the first and second end sides 120a, 120b.

More generally, any configuration with positioning members able to form stoppers away from the corner regions CR may be provided, so that a higher constraining effect can be obtained in a center of the pouch 2, as illustrated in FIGS. 9A-9B in particular. This is of interest for managing freeze/thaw operations of biopharmaceutical materials contained in the pouch 2. This is also of interest to better stacking the systems such as illustrated in FIGS. 4A and 6A, with higher compactness (less vertical space between two adjacent storage units 10), thus offering opportunities to store more pouches 2 in a freezing chamber.

Dashed lines in FIG. 9B show the kind of belly usually obtained when similarly allowing a significant stroke in each region of the peripheral margin 80. It is thus of interest to limit or prevent the displacement of the middle part of the protecting body 12, 112, 212, in order to limit accumulated mass (of important thickness) that could be difficult to be thawed.

FIG. 9A shows that the frame 15 or any kind of holding part of the assembly HR is suitable to allow the protecting body 12, 112, 212 to change its conformation (with decrease in body width and in body length), thus allowing reducing:
the pouch 2 in width (with w'<w, where w' is the pouch width in filled state, as compared to pouch width w in empty state), and
the pouch 2 in length (with L'<L, where L' is the pouch length in filled state, as compared to pouch length L in empty state).

In some variants, the positing members PM may be positioned in through slots and maintained stationary, for instance by being secured to or integral with the rigid frame 15 or similar holding and retaining assembly. The slots in the protecting body may be of greater size only near the end sides 120a, 120b, thus allowing greater shrinking only at the corner regions CR and preventing forming a too great bulge near the center C (due to belly effect/retention in the intermediate parts where the positioning members are early stopping members).

The holding and retaining assembly HR may comprise at least three positioning members PM distributed on each of the longitudinal sides 120c, 120d, with typically one or two central stoppers 41 corresponding to the positioning members PM arranged away from the corner regions CR.

Additionally or independently of having such belly retention effect, each system or at least one of a system amongst a stack of systems may be provided with a sample unit SU including the bag 2' where a small amount representative of the biopharmaceutical composition Q can be stored. At thawing stage, it may be of interest to have a sample unit SU providing a small amount of biopharmaceutical composition Q that has be submitted to same treatments, same freezing operations as the composition contained in the large capacity pouch 2. A small amount is faster to be heated, making the thawing operation quick for the content of the sample unit SU.

The system 1 is well adapted for freezing, storing and thawing biopharmaceutical materials contained in a flexible pouch 2 of simple conception. A storage unit 10 as above described is of interest for at least one of the following reasons:
accommodating and handling pouches of very large capacity, with minimizing one of the three dimensions (along Z-direction) of the storage unit 10,
obtain a predictable expansion of the pouch, while also having a gain in time for thawing and/or draining operations
conditioning the biopharmaceutical composition Q with a high level of protection, with optimized bulk.

In embodiments with the adjustable positioning members PM, the filling of the pouch 2 may be performed with a controlled and restricted expansion, so that expansion is restricted in one or more areas where the fluid thickness would reach a maximum if no expansion control is carried. The interior volume or cavity delimited by the main walls W1, W2 is expanded with prevention of free expansion in the middle areas of these walls W1, W2. Especially expansion can be limited along one or more belt line BL that joins the two intermediate parts 82, as illustrated in FIG. 9A.

Depression along such belt line BL, due to the low or inexistent shrink stroke in the intermediate parts 82, typically creates at least one recess. In the pouch 2 as filled and in containment configuration of the storage unit 10, at least one recess is thus created in the filled pouch 2 between the two bulges B1, B2. This allows a generally equal distribution of fluid, as a more uniform thickness distribution is obtained, without decreasing the capacity of the pouch 2.

The pouch 2 and the protecting body 12 may be exposed to a temperature of about −70° C. or lower to freeze the biopharmaceutical fluid/composition Q. The annular shape of the frame 15 of the holding and retaining assembly HR is of interest to provide a recessed area where cold air can circulate and flow between systems 1 (even if they are staked). But other shapes and structures may be used to form a holding and retaining assembly for a controlled expansion, in order to eliminate or reduce the formation of too significant projections during freezing.

The present invention has been described in connection with the preferred embodiments. These embodiments, however, are merely for example and the invention is not restricted thereto.

Of course, the pouches 2 of the present invention are not in any way limited to pouches having four sides and/or pouches that are larger than wide. The pouches 2 may have other shapes provided with two generally parallel sides, covered by the pair of plates 12A, 12B or similar protecting body including two flat portions. While each plate 12A or 12B is illustrated as a one-piece element, options are available for combining two or more flat containment pieces able to restrict expansion of the pouch 2, while being more or less displaceable for adjustment of the shrink stroke.

It will be understood by those skilled in the art that other variations and modifications can easily be made within the scope of the invention as claimed.

Any reference sign in the following claims should not be construed as limiting the claim. It will be obvious that the use of the verb "to comprise" and its conjugations does not exclude the presence of any other elements besides those defined in any claim. The word "a" or "an" preceding an element does not exclude the presence of a plurality of such elements.

The invention claimed is:

1. A system for conditioning a biopharmaceutical composition, for use in freezing, storing, and thawing the biopharmaceutical composition contained in a flexible pouch, the system comprising:
a protecting body comprising two plates for protecting the pouch, the protecting body comprising a longitudinal axis and four sides, the four sides comprising two longitudinal sides extending parallel to the longitudinal axis and two other sides;
an attachment system for fastening the two plates, the protecting body comprising a peripheral margin that extends annularly in a protecting body reference plane, the peripheral margin being provided with at least one opening configured to receive at least one port of the pouch;
positioning members that are secured to or formed on the peripheral margin; and
a frame, extending around a hollow space in which the pouch extends, the frame being distinct from the protecting body and provided with two longitudinal supporting profiles,
wherein the frame comprises abutment surfaces included and distributed in the two longitudinal supporting profiles, the positioning members connecting the peripheral margin to the two longitudinal supporting profiles of the frame so that the frame retains and supports:
the protecting body, and the pouch that is sandwiched between the two plates which constrain the pouch, wherein the positioning members are each slidably mounted in a profile cavity delimited by a corresponding one of the two longitudinal supporting profiles, in order to be movable along a direction transverse to the longitudinal axis, between:

a first position, in a non-filled-state of the pouch, in which the positioning members are pushed outwardly or maintained away from the abutment surfaces by the protecting body, so that the positioning members can be displaced inwardly, and a second position, in a filled-state of the pouch, in which the positioning members are each engaged against one of the abutment surfaces.

2. The system according to claim 1, wherein filling the pouch causes a conformation change of the protecting body with shrinking of the protecting body in the protecting body reference plane, said shrinking of the protecting body resulting from the positioning members passing from the first position to the second position.

3. The system according to claim 1, wherein the positioning members, which are distinct and separate from the pouch and from the plates, are configured to protrude each from at least one amongst a lower surface and an upper surface of the protecting body, in the peripheral margin.

4. The system according to claim 3, wherein the positioning members are provided with one or more plug parts, in order to be removably plugged on the peripheral margin.

5. The system according to claim 4, wherein the positioning members comprise each a lower part and an upper part that are two separate pieces configured to sandwich the protecting body, in a region of the peripheral margin.

6. The system according to claim 1,
wherein the positioning members comprise each a lower part and an upper part that are two separate pieces configured to sandwich the protecting body, in a sandwiching region of the peripheral margin, each sandwiching region being:
elongated parallel to a protecting body edge,
at least four times longer than a maximal width of the positioning members.

7. The system according to claim 3,
wherein the positioning members are part of the attachment system, and
wherein the positioning members support or include each an insert piece engaged in the protecting body through thickness of the peripheral margin.

8. The system according to claim 1, wherein the positioning members are distributed at different longitudinal locations along the longitudinal axis.

9. The system according to claim 1,
wherein the abutment surfaces are included in abutment members which extend transversely relative to the protecting body reference plane, and
wherein each of the abutment members is configured to separate the hollow space from a cavity where at least one of the positioning members extend.

10. The system according to claim 1, wherein the frame comprises pieces, each interposed between two perpendicular profiles of the frame, forming respective corner parts of the frame.

11. The system according to claim 1,
wherein the two plates are two pieces, the two longitudinal supporting profiles being made of other pieces that are each:
C-shaped or U-shaped to delimit associated profile cavity, and
only covering the protecting body at the peripheral margin.

12. The system according to claim 1,
wherein the frame is further provided with one or two transverse supporting parts that are rigid and separate from the positioning members, and
wherein each of the one or two transverse supporting parts is housing additional positioning members that are each slidably mounted on or in a corresponding transverse supporting part, in order to be movable along direction of the longitudinal axis.

13. The system according to claim 12,
wherein the frame has a rectangular shape thanks to the two longitudinal supporting profiles and the two transverse supporting parts, and
wherein the frame comprises additional abutment surfaces included and distributed in the two transverse supporting parts, the additional positioning members being movable along direction of the longitudinal axis between:
a first position, in a non-filled-state of the pouch, in which the additional positioning members are pushed outwardly or maintained away from the additional abutment surfaces by the protecting body, so that the additional positioning members can be displaced inwardly due to a conformation change of the protecting body, and
a second position, in a filled-state of the pouch, in which the positioning members are each engaged against one of the additional abutment surfaces.

14. The system according to claim 12,
wherein the protecting body has a rectangular shape with four corner regions away from a middle region of the protecting body, and
wherein at least four corner positioning members, chosen amongst the positioning members and the additional positioning members, are distributed at respective ends of the two longitudinal supporting profiles and at respective ends of the two transverse supporting parts, in order to increase shrinking of the protecting body in the protecting body reference plane in each of the four corner regions during filling of the pouch.

15. The system according to claim 1, wherein the frame is made of a material chosen amongst steel, metal or rigid plastic and has four sides assembled after fastening of the two plates, so that the frame is of rectangular shape.

16. The system according to claim 1, further comprising:
biasing members that are configured to exert a return action for displacing the positioning members outwardly toward the first position which is a by-default-position in non-filled state and in an emptied state of the pouch,
wherein filling of the pouch causes progressive deformation of the protecting body, in order to create in the protecting body reference plane a pulling action to pull the positioning members inwardly, the pulling action increasing with level of filling of the pouch and being opposite to the biasing action of the return members.

17. The system according to claim 1, wherein all or part of the positioning members are provided with contact parts in contact with the abutment surfaces in the second position, the contact parts being biasing members configured to exert a return action for displacing the positioning members outwardly toward the first position which is a by-default-position in non-filled state and in an emptied state of the pouch.

18. The system according to claim 1, further comprising:
pull elements that are displaceable transversely relative to the two longitudinal supporting parts and coupled to portions of the peripheral margin,
wherein the pull elements are configured to pull all or part of the peripheral margin outwardly when the pull elements are displaced from a retracted position to an expanded position.

19. A method of assembling a system as recited in claim 1, which is a protection system for storing and withstanding freezing and thawing of the biopharmaceutical composition contained in the pouch of the freeze/thaw containment system, the method comprising:
sandwiching a flexible pouch between two plates of a protecting body, selectively by a covering portion distributed in the two plates for covering the flexible pouch, the protecting body being configured for protecting the flexible pouch and comprising the two plates, the protecting body further having a longitudinal axis and comprising four sides, the four sides comprising two longitudinal sides extending parallel to the longitudinal axis and two other sides; and
using an attachment device for fastening the two plates so that in an assembled state of the two plates, the protecting body comprises a peripheral margin that extends annularly in a protecting body reference plane, around the covering portion, the peripheral margin being provided with:
at least one opening receiving at least one port of the flexible pouch, and
positioning members that are secured to or formed on the peripheral margin,
wherein, in the assembled state of the two plates, a frame is mounted around the protecting body, by coupling two longitudinal supporting profiles that are distinct from the protecting body to the peripheral margin, the two longitudinal supporting profiles extending parallel to the longitudinal axis when coupled to the peripheral margin, in order to form two opposite sides of the frame, the positioning members connecting the peripheral margin to the two longitudinal supporting profiles of the frame,
wherein abutment surfaces are included and distributed in the two longitudinal supporting profiles, so that the frame retains and supports:
the protecting body, and
the pouch that is sandwiched between the two plates which constrain the pouch,
and wherein the positioning members are each slidably mounted in a profile cavity delimited by a corresponding one of the two longitudinal supporting profiles during mounting of the frame, in order to be movable along a direction transverse to the longitudinal axis between:
a first position, in a non-filled-state of the pouch, in which the positioning members are pushed outwardly or maintained away from the abutment surfaces by the protecting body, and
and a second position, in a filled-state of the pouch, in which the positioning members are each engaged against one of the abutment surfaces.

20. The system according to claim 1, wherein the two longitudinal supporting profiles delimit two opposite elongated cavities, which are each housing several of the positioning members.

* * * * *